United States Patent [19]

Sanchez et al.

[11] Patent Number: 5,760,149
[45] Date of Patent: Jun. 2, 1998

[54] POLY(MONOPEROXYCARBONATES)

[75] Inventors: Jose Sanchez, Grand Island; John Salvatore Yormick, Kenmore, both of N.Y.; Jerome Wicher, Collegeville; Kenneth George Malone, Plymouth Meeting, both of Pa.

[73] Assignee: Elf Atochem North America, Inc., Philadelphia, Pa.

[21] Appl. No.: 907,558

[22] Filed: Aug. 8, 1997

Related U.S. Application Data

[60] Provisional application No. 60/025,206 Sep. 23, 1996.

[51] Int. Cl.$^6$ .................... C08F 4/36; C08F 4/38; C08F 8/00; C07C 69/96
[52] U.S. Cl. .................... 526/230.5; 525/313; 525/387; 525/451; 526/346; 558/263
[58] Field of Search .................... 558/263; 526/230.5, 526/346; 525/313, 387, 451

[56] References Cited

U.S. PATENT DOCUMENTS

| | | |
|---|---|---|
| 3,652,631 | 3/1972 | Stevens et al. . |
| 4,136,105 | 1/1979 | Sanchez . |
| 5,266,603 | 11/1993 | Holzmeier et al. . |
| 5,314,970 | 5/1994 | MacLeay et al. . |
| 5,446,191 | 8/1995 | Suyama et al. . |
| 5,455,321 | 10/1995 | Cummings et al. . |

OTHER PUBLICATIONS

92:164324 Chem. Abs. Jun. 1980 Ladousse et al.
71:123928 Chem. Abs. Dec. 1969 Komai et al.
99:88729 Chem. Abs. Nov. 1983 Sanken Kako Co.

*Primary Examiner*—Michael G. Ambrose
*Attorney, Agent, or Firm*—Stanley A. Marcus; Royal E. Bright

[57] ABSTRACT

Poly(monoperoxycarbonates) of the structure:

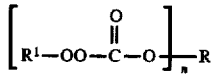

where R, $R^1$ and n are defined in the summary of the invention such as 1,1,1-tris(t-butylperoxycarbonyloxymethyl)ethane, intermediates for their preparation as well as processes for their preparation and use are disclosed. The monoperoxycarbonate compounds are useful in initiating the polymerization of ethylenically unsaturated monomers, particularly styrene, curing of unsaturated polyester resins, and in modifying the molecular weight of polymers such as by crosslinking or controlled chain degradation.

20 Claims, No Drawings

POLY(MONOPEROXYCARBONATES)

This Application claims priority from Provisional Application Ser. No. 60/025,206, filed Aug. 23, 1996.

BACKGROUND OF THE INVENTION a) Field of the Invention

This invention relates to new and novel compositions of matter classified in the art of chemistry as poly (monoperoxycarbonate) compounds of Structure A:

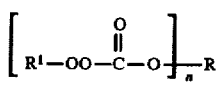

[The definitions of n, R and $R^1$ are given in the SUMMARY OF THE INVENTION], to processes for their preparation and use and to intermediates used in the preparation processes.

There is a need in the polymer industry for efficient, free-radical initiators for polymerizing ethylenically unsaturated monomers, such as styrene, at faster production rates while retaining polymer molecular weight and polymer physical properties, e.g., tensile properties. In general, use of more active free-radical initiators and increase of polymerization temperatures to enhance production rates of polymers (e.g., polystyrene) result in the desired enhancement of production rates but also undesirably result in reduced polymer molecular weights and reduced tensile properties. There also is a need to increase the molecular weight of commercial polymers in order to enhance polymer physical properties. Reduction of polymerization temperatures, reduction in initiator use levels and use of less active initiators generally achieve the goal of increasing polymer molecular weight, however, polymer production rates are reduced. In the 1980s, the art of polymerizing styrene was advanced. Use of diperoxyketals, such as 1,1-bis(t-butylperoxy)cyclohexane, as initiators in place of standard initiators, such as dibenzoyl peroxide and t-butyl peroxybenzoate, for commercial styrene polymerizations resulted in enhanced polystyrene molecular weight and/or enhanced production of polystyrene. The current applicants further advanced the art and found that the novel poly (monoperoxycarbonate) compositions of Structure A of this invention can be used as initiators for polymerizing ethylenically unsaturated monomers to produce polymers (e.g., polystyrene) having significantly increased polymer molecular weights while simultaneously retaining or increasing polymerization rates or to produce polymers at significantly enhanced rates while retaining polymer molecular weights, and that the compositions of the instant invention were superior to diperoxyketals, such as 1,1-bis (t-butylperoxy)cyclohexane. Thus, the novel poly (monoperoxycarbonate) compositions of the instant invention are capable of satisfying the polymerization needs of polymer industry.

There also is a need in the polyester industry for free-radical initiators that cure unsaturated polyester resins faster and/or at lower temperatures. The novel poly (monoperoxycarbonate) compositions of the instant invention are also capable of satisfying this polymer industry need.

b) Description of the Prior Art

U.S. Pat. No. 3,652,631 (to PPG, Mar. 28, 1972) discloses bis(monoperoxycarbonates 1 derived from t-butyl hydroperoxide,

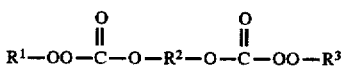

(where $R^1$ and $R^3$ are alkyl up to 10 carbons, optionally substituted with halogen or nitro groups, and $R^2$ is the divalent residue of an organic diol containing up to 12 carbon atoms and up to three ether linkages), t-amyl hydroperoxide or t-hexyl hydroperoxide and bis (chloroformates) and the use of these compositions to polymerize monomers such as styrene. The bis (monoperoxycarbonate) composition, 1,5-bis(t-butylperoxycarbonyloxy)-3-oxapentane, is covered by U.S. Pat. No. 3,652,631. The applicants of the instant invention found that the novel poly(monoperoxycarbonate) compositions of Structure A were better initiators for polymerizing styrene than 1,5-bis(t-butylperoxycarbonyloxy)-3-oxapentane as they produced polystyrenes with significantly increased molecular weights under the same polymerization conditions.

U.S. Pat. No. 4,136,105, Jan. 23, 1979 (to Pennwalt Corp.) discloses O-alkyl OO-t-octyl monoperoxycarbonates 2,

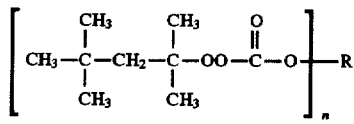

(where n is an integer from 1 to 4, preferably 1; when n is 1, R is selected from alkyl of 1–16 carbons, cycloalkyl of 5–12 carbons, aryl of 6 to 14 carbons, aralkyl of 7–14 carbons, alkenyl of 3–10 carbons, cycloalkenyl of 5–10 carbons, and alkynyl of 3–14 carbons; when n is 2, R is selected from alkylene of 2–12 carbons, cycloalkylene of 4–12 carbons, arylene of 6–14 carbons, alkenylene of 2–12 carbons, alkynylene of 4–12 carbons, methylenephenylmethylene, methylenecyclohexylmethylene, —$R^1XR^1$—, and —$R^2YR^2$—, where $R^1$ is alkylene of 2–6 carbons, $R^2$ is phenylene, X is —O— or —S—, and Y is —O—, —S—, —$CH_2$— or —$C(CH_3)_2$—; when n is 3, R is $R^3C(CH_2$—$)_3$, —$CH(CH_2$—$)_2$, and —$CH_2CH$(—) $CH_2CH_2CH_2CH_2$—, where $R^3$ is alkyl of 1–5 carbons; and when n is 4, R is $C(CH_2$—$)_4$.)

and the use of these compositions for initiating the polymerization of vinyl monomers and for curing of unsaturated polyester resins. This art covers tris- and tetrakis(mono-t-octylperoxycarbonates) derived from t-octyl hydroperoxide but does not disclose the novel poly(monoperoxycarbonate) compositions of the instant invention that are derived from t-butyl and t-amyl hydroperoxides.

U.S. Pat. No. 5,314,970, (to Elf Atochem, May 24, 1994) discloses OO-t-alkyl O-polycaprolactone monoperoxycarbonates, i.e., polycaprolactones end-capped with OO-t-alkylperoxycarbonate groups 3 derived from t-alkyl hydroperoxides and chloroformates of

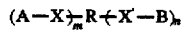

(where A is 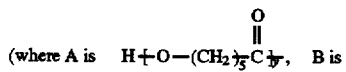, B is

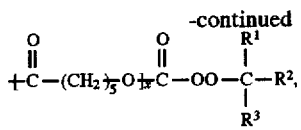

m is an integer from 0 to 3, n is an integer from 1 to 4, m+n is an integer from 1 to 4, $R^1$ and $R^2$ are the same or different and are alkyl of 1 to 4 carbons, $R^3$ is alkyl of 1 to 12 carbons or alkynyl of 2 to 12 carbons, y is an integer from 0 to about 10,000, x is an integer from 4 to about 22,000, (y)(m)+(x)(n) is an integer from 4 to about 22,000, X and X' are independently selected from —O— or —N($R^4$—), $R^4$ being hydrogen, substituted or unsubstituted aliphatic of 1 to 20 carbons, substituted or unsubstituted acyclic of 5 to 18 carbons, substituted or unsubstituted aromatic of 6–14 carbons, and substituted or unsubstituted araliphatic of 7 to 22 carbons, and R is a substituted or unsubstituted aliphatic, alicyclic aromatic or araliphatic radical, diradical, triradical or tetraradical), hydroxy-terminated polycaprolactones and the use of these compositions for initiating the polymerization of vinyl monomers, for curing of unsaturated polyester resins, for preparing polycaprolactone block copolymers, for crosslinking polyolefins, for curing of elastomers, for modifying polypropylene, for grafting polycaprolactone blocks onto polyolefins, for preparation of interpenetrating polymer networks, and for preparation of graft polyols.

The only monoperoxycarbonate compositions that were disclosed in the examples were bis(t-butyl monoperoxycarbonates) and bis(t-amyl monoperoxycarbonates) derived from diols. The only utility disclosed in the examples and the utility emphasized in the abstract, the specification and the claims was the use of the bis(monoperoxycarbonates) for preparing polycaprolactone-polystyrene block and graft copolymers for use as compatibilizing agents for blends of polymers. Since the most effective block copolymers for compatibilizing polymer blends were those with larger block segments, the most preferred poly(e-caprolactones) were dihydroxy-terminated poly(e-caprolactones) of approximately 3,000 to 15,000 molecular weight (U.S. Pat. No. 5,314,970, column 12, lines 30–33). The hydroxy-terminated poly(e-caprolactone) starting materials of the instant invention are confined to polyhydroxy-terminated poly(e-caprolactones) except in the special cases when novel peroxide-substituted bis (monoperoxycarbonates) are made by reacting the bis (haloformates) of bishydroxy-terminated poly(e-caprolactones with 1,1,4-trimethyl-4-(t-butylperoxy)pentyl hydroperoxide or with 1,1,4-trimethyl-4-(t-amylperoxy) pentyl hydroperoxide. Furthermore, the polyhydroxy starting materials (i.e., diols, triols and higher polyols) for the compositions of the instant invention must have molecular weights of less than about 1000, less than about 1000 and less than about 1300, respectively.

U.S. Pat. No. 5,314,970 suggests no advancement in the art of polymerizing styrene with the bis (monoperoxycarbonate) compositions of the patent. The bis(t-butyl monoperoxycarbonate) derived from TONE® 200 is a composition of U.S. Pat. No. 5,314,970. The applicants of the instant invention found that the novel poly(monoperoxycarbonate) compositions of Structure A were better initiators for polymerizing styrene as they produced polystyrenes with significantly higher molecular weights under the same polymerization conditions than were produced with the bis(t-butyl monoperoxycarbonate) of TONE® 200.

U.S. Pat. No. 5,455,321 (to The Dow Chemical Company, Oct. 3, 1995) discloses a process for producing a monovinylidene aromatic polymer (e.g., polystyrene) having molecular weight greater than 275,000 which comprises polymerizing a monovinylidene aromatic monomer (e.g., styrene) in the presence of, a) 10 to 2000 ppm by weight of at least one free-radical generating, branching polymerization initiator of the structure:

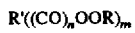

where n is 0 or 1, m is 3 to 6, R' is a multifunctional organic radical of up to 25 non-hydrogen atoms, and R is $C_{1-15}$ tertiary alkyl or $C_{7-15}$ tertiary aralkyl groups, and, b) 10 to 2000 ppm of one or more organic gel-reducing agents selected from the group consisting of I) mercaptans, terpenes, halocarbons and halohydrocarbons having up to 20 carbons, ii) a recycle liquid generated by devolatilization of the polymerized monomer mixture, and, iii) mixture of the organic gel-reducing agents from I) and ii). A preferred free-radical generating, branching polymerization initiator was 2,2-bis(4,4-di-t-butylperoxycyclohexyl)propane:

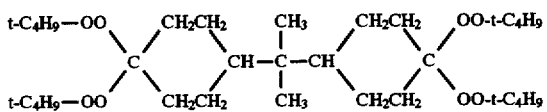

Other free-radical generating, branching polymerization initiators disclosed by this patent were tri-t-alkyl 1,3,5-benzenetricarboperoxoic acid esters, tetra-t-alkyl 1,2,4,5-benzenetetracarboperoxoic acid esters and 2,4,6-tri-t-alkylperoxy-1,3,5-triazines, 2-(4-isopropenylphenyl)-2-propyl t-alkyl peroxides, t-alkyl 4-isopropenylperoxybenzoates, di-t-alkyl diperoxymaleates and diperoxyfumarates, and OO-t-alkyl O-alkyl monoperoxymaleates and monoperoxyfumarates. U.S. Pat. No. 5,455,321 does not disclose the novel poly (monoperoxycarbonates) of the instant invention nor the novel processes using them in polymer applications.

U.S. Pat. No. 5,266,603 (to Huels Aktiengesellschaft, Nov. 30, 1993) discloses a process for the production of expandable styrene homopolymers or copolymers by a) providing an aqueous suspension of styrene monomer and a peroxide initiator system comprising at least one aliphatic or cycloaliphatic diperoxyketal (e.g., 2,2-bis(t-butylperoxy) butane or 1,1-bis(t-butylperoxy)cyclohexane) or monoperoxycarbonate initiator (e.g., OO-t-butyl O-(2-ethylhexyl) monoperoxycarbonate or OO-t-amyl O-(2-ethylhexyl) monoperoxycarbonate) and a peroxide initiator having a shorter half-life than an aliphatic or cycloaliphatic diperoxyketal or monoperoxycarbonate initiator (e.g., dibenzoyl peroxide), b) heating the stirred suspension from 80° C. to 100° C. for a first period of time to effect initial polymerization, c) adding a $C_{3-6}$ hydrocarbon propellant to the stirred suspension, d) increasing the temperature of the resulting suspension to a temperature from 100° C. to 130° C. for a second period of time to effect final polymerization and produce an expandable polystyrene resin. In this patent, no bis-, tris- or higher poly(monoperoxycarbonates) are employed, only mono(monoperoxycarbonates) such as OO-t-butyl O-(2-ethylhexyl) monoperoxycarbonate or OO-t-amyl O-(2-ethylhexyl) monoperoxycarbonate.

As a whole, the above art does not disclose the poly (monoperoxycarbonate) compositions of Structure A.

c) Definitions

A diol is defined as the structure R(—OH)$_2$, where R is a diradical, e.g., R(—)$_2$. A triol is defined as the structure R(—OH)$_3$, where R is a triradical, e.g., R(—)$_3$. A polyol is defined as a structure R(—OH)$_n$, where R is a polyradical, e.g., R(—)$_n$, and n is an integer $\geq 2$. A tetraol is defined as the structure R(—OH)$_4$, where R is a tetraradical, e.g., R(—)$_4$.

When any generalized functional group or index, such as R, R$^1$, R$^2$, x, n, etc., appears more than once in a general formula or structure, the meaning of each is independent of one another.

SUMMARY OF THE INVENTION

The invention provides in its first composition aspect, a poly(monoperoxycarbonate) compound of Structure A:

A where n is an integer from 3 to 8, R$^1$ is selected from the group consisting of t-alkyl radicals of 4 to 12 carbons, 1,1,4-trimethyl-4(t-butylperoxy)pentyl radical, 1,1,4-trimethyl-4(t-amylperoxy)pentyl radical, t-cycloalkyl radicals of 6 to 10 carbons, t-aralkyl radicals of 9 to 13 carbons and 3-methyl-1-butyn-3-yl and 3-methyl-1-pentyn-3-yl, and with the proviso that when R$^1$ is selected from 1,1,4-trimethyl-4(t-butylperoxy)pentyl radical and 1,1,4-trimethyl-4(t-amylperoxy)pentyl radical, n can also have a value of 2;

when n is 2, R is a diradical selected from alkylene of 2 to 12 carbons, alkenylene of 4 to 8 carbons and diradical structures (n) and (o),

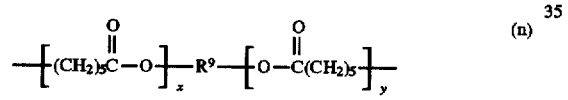 (n)

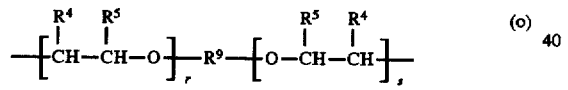 (o)

where R$^9$ is an alkylene diradical of 2 to 8 carbons; when n is 3, R is a triradical selected from 1,3,5-cyclohextriyl, R$^2$C(CH$_2$—)$_3$, —CHR$^2$CH(—)CH$_2$— and structures (a), (b), (c), (d) and (e), —CH$_2$—CH—CH$_2$CH$_2$—, (a)
  |

—CH$_2$—CH—CH$_2$CH$_2$CH$_2$CH$_2$—, (b)
  |

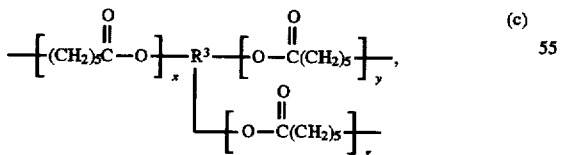 (c)

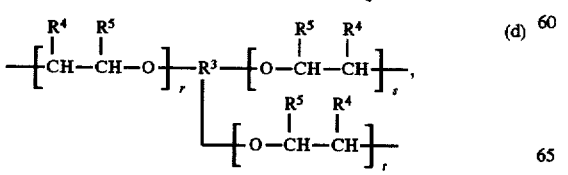 (d)

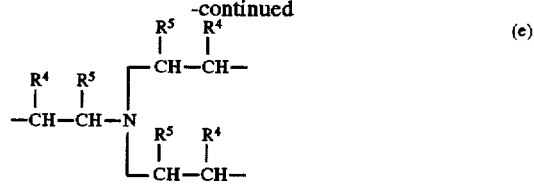 (e)

where R$^2$ is selected from hydrogen and an alkyl radical of 1 to 6 carbons, R$^3$ is a triradical selected from the group consisting of R$^2$C(CH$_2$—)$_3$, —CHR$^2$CH(—)CH$_2$— and structures (a) and (b), R$^4$ and R$^5$ are the same or different and are selected from hydrogen and alkyl radicals of 1 to 4 carbons, x, y and z are integers from 0 to 5 with the proviso that the sum of x, y and z is from 2 to 8, and r, s and t are integers from 0 to 6 with the proviso that the sum of r, s and t is from 3 to 18, and when n is 4 to 8, R is a polyradical selected from C(CH$_2$—)$_4$ and structures (f), (g), (h), (i), (j), (k) and (l),

 (f)

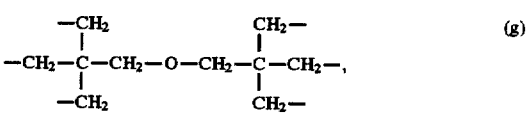 (g)

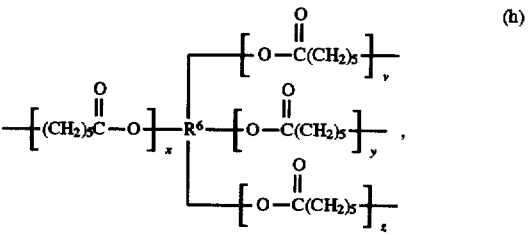 (h)

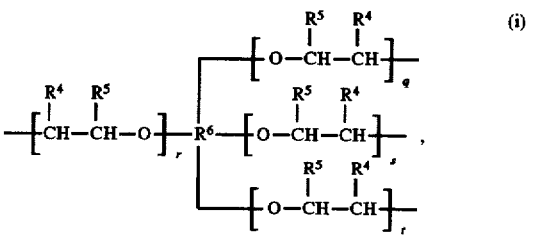 (i)

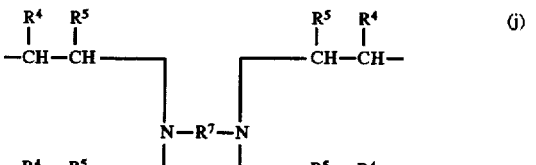 (j)

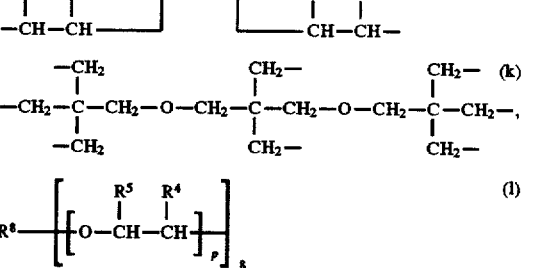 (k)

(l)

where R$^6$ is a tetraradical selected from C(CH$_2$—)$_4$ and structure (f), R$^7$ is a diradical selected from alkylene of 2 to 6 carbons and 1,2-, 1,3- and 1,4-phenylene, $R^8$ is the sucrose-based octaradical of structure (m),

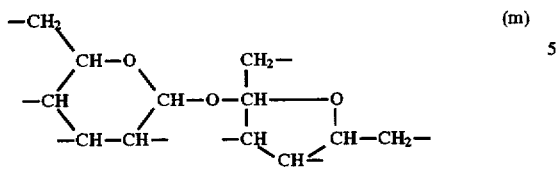

p is an integer from 1 to 3, v is an integer from 0 to 5 with the proviso that the sum of v, x, y and z is from 3 to 10, and q is an integer from 0 to 4 with the proviso that the sum of q, r, s and t is from 2 to 16, and with the further proviso that when R is $R^3C(CH_2—)_3$, structure (b) or $C(CH_2—)_4$, $R^1$ is not t-octyl; such novel poly (monoperoxycarbonate) of Structure A being synthesized from a diol, trial or a higher polyol of Structure AA:

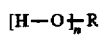 AA having a molecular weight of less than about 1000, less than about 1000 or less than about 1300, respectively.

The invention provides in a subgeneric composition aspect, a compound of Structure A' wherein in Structure A, when n is 3, R is a triradical selected from 1,3,5-cyclohextriyl, $R^2C(CH_2—)_3$, —$CHR^2CH(—)CH_2—$, and structures (a), (b), (d) and (e) as defined above.

The invention provides in a second subgeneric composition aspect, a compound of Structure A" wherein in Structure A when n is 3, R is as defined above for the first subgeneric composition aspect of the invention and when n is 4 to 8, R is a polyradical selected from $C(CH_2—)_4$, and structures (f), (g), (i), (j), (k) and (l) as defined above.

The compositions of the first composition aspect of the invention have the inherent physical properties of being amorphous solids or viscous liquids said solids being white to light straw colored and said liquids being colorless to light straw colored. The solids exhibit melting ranges and all compositions exhibit infra red spectra and peroxide active oxygen content positively confirming the structures sought to be patented.

The compositions of the first composition aspect of the invention possess the inherent applied use characteristic of being initiators for the polymerization of ethylenically unsaturated monomers, particularly styrene and for the modification of the molecular weight of polymers such as unsaturated polyesters, thermoplastic polymers, elastomeric polymers and mixtures of such polymers.

The invention provides in a first process aspect, a process for free-radical initiated modification of a substrate selected from the group consisting of ethylenically unsaturated monomers, and polymers susceptible to free radical induced molecular weight modification which comprises the treatment of said substrates under conditions effective to initiate free radical induced modification of said substrates with one or more compounds of Structure (A) in effective initiating amounts.

Special mention is made of the following free radical induced molecular weight modification processes:

a. polymerizing ethylenically unsaturated monomer compositions (such as styrene, ethylene, allyl diglycol carbonate (ADC), and the like known to the art as susceptible to such polymerization), optionally in the presence of an unsaturated elastomer (such as polybutadiene, polyisoprene, and the like known in the art to be useful when present in such polymerizations), b. curing of unsaturated polyester resin compositions, c. crosslinking and curing of thermoplastic polymer and elastomeric polymer compositions, and, e. modifying the molecular weight of polyolefin compositions, The invention provides in a second process aspect, a process for free-radical initiated polymerization of ethylenically unsaturated monomer compositions (such as styrene, ethylene, allyl diglycol carbonate (ADC), and the like), known in the art to be susceptible to such polymerization optionally in the presence of an unsaturated elastomer (such as polybutadiene, polyisoprene, and the like), known in the art to be useful when present in such polymerizations under conditions effective to initiate free-radical induced polymerization, with one or more compounds of Structure A in combination with other free-radical initiators selected from the group consisting of monoperoxides and diperoxides (such as diacyl peroxides, diperoxyketals, peroxyesters, monoperoxycarbonates and dialkyl peroxides), in effective initiating amounts.

DETAILED DESCRIPTION OF THE PREFERRED EMBODIMENTS

Novel Poly(monoperoxycarbonate) Compositions of Structure A—Preparative Methods The novel poly(monoperoxycarbonate) compositions of Structure A can be prepared by reacting one or more t-alkyl hydroperoxides of Structure B.

 B with poly(haloformates) of Structure C, at –30° C. to 50° C.,

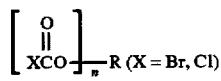 C wherein R, $R^1$ and n are as defined for Structure A optionally in the presence of an inorganic or organic base, and optionally in the presence of one or more solvents. Non-limiting examples of suitable optional bases include triethylamine, tributylamine, N,N-diisopropylethylamine, 2,2,6,6-tetramethylpiperidine, N,N-dimethylaniline, N,N-dimethylaminopyridine, 2,4,6-colidine, urea, tetramethylurea, sodium hydroxide, sodium carbonate, sodium hydrogen carbonate, potassium hydroxide, potassium carbonate, potassium hydrogen carbonate, calcium hydroxide, magnesium hydroxide, barium hydroxide, calcium carbonate and trisodium phosphate.

Non-limiting examples of suitable optional solvents include pentane, hexanes, heptanes, dodecanes, odorless mineral spirits mixtures, toluene, xylenes, cumene, methylene chloride, ethyl acetate, 2-ethylhexyl acetate, isobutyl isobutyrate, dimethyl adipate, dimethyl succinate, dimethyl glutarate (or mixtures thereof), dimethyl phthalate, dibutyl phthalate, benzyl butyl phthalate, diethyl ether, methyl t-butyl ether (MTBE), 2-methoxyethyl acetate, tetrahydrofuran (THF) and others.

The suitable hydroperoxides of Structure B that can be reacted with poly(haloformates) of Structure C include t-butyl hydroperoxide, t-amyl hydroperoxide, 2-methyl-2-pentyl hydroperoxide, 3-methyl-3-pentyl hydroperoxide, 3-methyl-1-butyn-3-yl hydroperoxide, 3-methyl-1-pentyn- 3-yl hydroperoxide, 2-methyl-2-hexyl hydroperoxide, 1,1,3,3-tetramethylbutyl hydroperoxide, 1,1,4-trimethyl-4(t-butylperoxy)pentyl hydroperoxide, 1,1,4-trimethyl-4(t-amylperoxy)pentyl hydroperoxide, 1-methyl-1-cyclohexyl hydro-peroxide, paramenthane hydroperoxide, α-cumyl hydroperoxide, 4-methyl-α-cumyl hydroperoxide, 3-methyl-α-cumyl hydroperoxide and diisopropylbenzene monohydroperoxide.

Non-limiting examples of suitable poly(haloformates) of Structure C that can be reacted with hydroperoxides of Structure B include 1,1,1-tris(chlorocarbonyloxymethyl)ethane, 1,1,1-tris-(chlorocarbonyloxymethyl)propane, 1,1,1-tris(chlorocarbonyloxymethyl)butane, 1,2,3-tris(chlorocarbonyloxy)propane, 1,2,3-tris(chlorocarbonyloxy)hexane, 1,2,3-tris(chlorocarbonyloxy)heptane, 1,2,4-tris(chlorocarbonyloxy)butane, 1,2,6-tris(chlorocarbonyloxy)hexane, 1,3,5-tris(chlorocarbonyloxy)cyclohexane, tetrakis(chlorocarbonyloxymethyl)methane, 1,2,3,4-tetrakis(chloro-carbonyloxy)butane, 1,1,1,5,5,5-hexa(chlorocarbonyloxymethyl)-3-oxapentane, and 1,1,1,5,5,9,9,9-octa(chlorocarbonyloxymethyl)-3,7-dioxanonane.

Also included as suitable poly(haloformates) of Structure C are tris- and tetrakis(chloroformates) of Structures D and E:

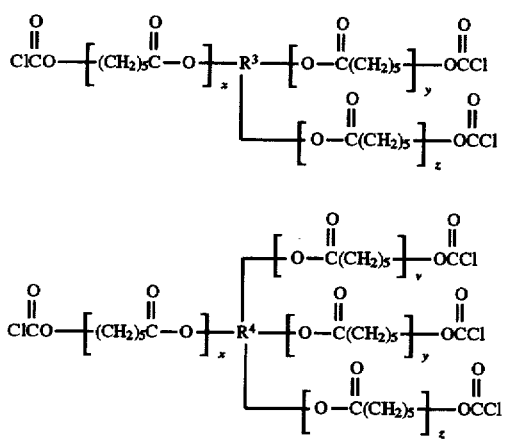

that are derived from polycaprolactone triols and tetraols (Structures F and G, respectively);

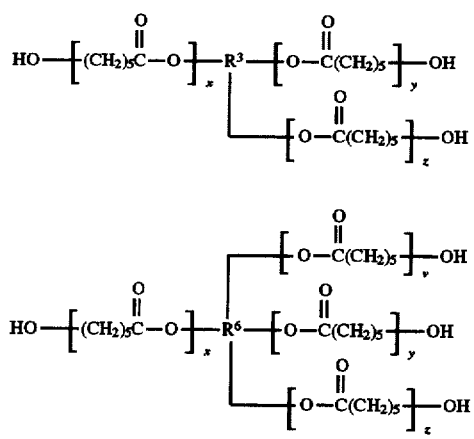

such as those manufactured by Union Carbide Corporation and sold using the trade name TONE®, e.g., TONE® 0301, TONE® 1303, TONE® 0305, TONE® 0310 and TONE® 4411), and tris- and tetrakis(chloroformates) of Structures H and I:

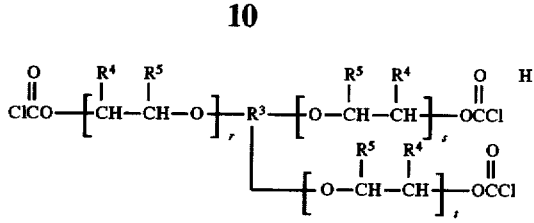

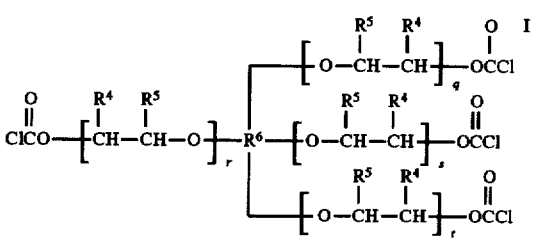

that are derived from polyether triols and tetraols (Structures J and K, respectively);

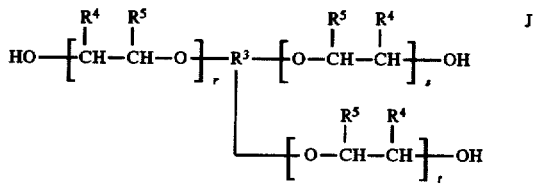

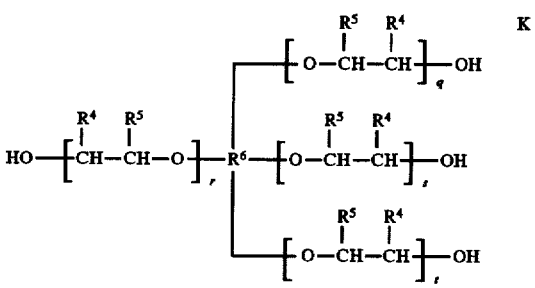

some of which are manufactured by BASF Corporation under the trade name PLURACOL®; where $R^4$ is methyl and $R^5$ is hydrogen, e.g., PLURACOL® GP-730, PLURACOL® TP-740, PLURACOL® PeP 450, PLURACOL® PeP 550 and PLURACOL® PeP 650, and others which are manufactured by the Dow Chemical Company under the trade name VORANOL®; such as Structure J, where $R^4$ and $R^5$ are hydrogen, e.g., VORANOL® 234–630, and still others which are manufactured by Arco Chemical Company under the trade name ARCOL®; such as Structure J where $R^4$ is methyl and $R^5$ is hydrogen, e.g., ARCOL® LG-650 and ARCOL® LHT-240. The molecular weights of the TONE®, PLURACOL®, VORANOL® and ARCOL® polyols as stated by the manufacturers are given below:

| POLYOL | TYPE | STRUCTURE | MOLECULAR WEIGHT |
|---|---|---|---|
| TONE ® 0301 | Triol | F | 300 |
| TONE ® 1303 | Triol | F | 425 |
| TONE ® 0305 | Triol | F | 540 |
| TONE ® 0310 | Triol | F | 900 |
| TONE ® 4411 | Tetraol | G | 1006 |
| PLURACOL ® GP-730 | Triol | J | 730 |
| PLURACOL ® TP-740 | Triol | J | 730 |
| PLURACOL ® PeP 450 | Tetraol | K | 405 |
| PLURACOL ® PeP 550 | Tetraol | K | 500 |
| PLURACOL ® PeP 650 | Tetraol | K | 594 |

| POLYOL | TYPE | STRUCTURE | MOLECULAR WEIGHT |
|---|---|---|---|
| VORANOL® 234-630 | Triol | J | 267 |
| ARCOL® LG-650 | Triol | J | 260 |
| ARCOL® LHT-240 | Triol | J | 700 |

When $R^1$ of Structure A is 1,1,4-trimethyl-4(t-butylperoxy)pentyl radical or 1,1,4-trimethyl-4(t-amylperoxy)pentyl radical and n is 2, bis(haloformates) derived from diols can be used to produce polyperoxide compositions of Structure A. Non-limiting examples of diol precursors to the bis(haloformates) include ethylene glycol, 1,2- and 1,3-propylene glycols, 2,2-dimethyl-1,3-propanediol, 1,4-butanediol, diethylene glycol, triethylene glycol, dipropylene glycol, 1,4-cyclohexanedimethanol, TONE® diols and others.

The definitions of $R^3$, $R^6$, q, r, s, t, v, x, y, and z are given in the SUMMARY OF THE INVENTION section.

The above poly(haloformates) can be prepared by reacting 0% to 100% excess carbonyl dihalides (such as the dibromide or the dichloride, i.e., phosgene) with the corresponding polyol, i.e., $(HO)_nR$, in the presence or absence of a tetraalkylurea (e.g., tetramethylurea), in the presence or absence of a solvent, until the reaction is completed. The excess carbonyl dibromide or phosgene is removed by stripping or by distillation. Non-limiting examples of suitable polyols that react with carbonyl dihalides to form the tri- and poly(haloformates) of Structure C include 1,1,1-tris(hydroxymethyl)ethane, 1,1,1-tris(hydroxymethyl)propane, 1,1,1-tris(hydroxymethyl)butane, glycerol, 1,2,3-trihydroxyhexane, 1,2,3-trihydroxyheptane, 1,2,4-trihydroxy-butane, 1,2,6-trihydroxyhexane, 1,3,5-trihydroxycyclohexane, pentaerythritol, 1,2,3,4-tetrahydroxybutane, 1,1,1,5,5,5-hexa(hydroxy-methyl)-3-oxapentane, 1,1,1,5,5,9,9,9-octa(hydroxymethyl)-3,7-dioxanonane, and polycaprolactone triols and tetraols of Structures F and G, respectively, and polyether triols and tetraols of Structures J and K, respectively.

Alternately, the novel poly(monoperoxycarbonate) compositions of Structure A can be prepared by reacting t-alkylperoxy haloformates of Structure L,

R¹—OO—CX [where X = Br or Cl]

with a polyol, i.e., $(HO)_nR$, in the presence of an inorganic or organic base, and optionally in the presence one or more solvents. The t-alkylperoxy haloformates of Structure L can be prepared by reacting a t-alkyl hydroperoxide of Structure B with excess carbonyl dihalide (carbonyl dibromide or phosgene) and removal of excess carbonyl dihalide by stripping or distillation.

Non-limiting examples of inorganic or organic bases, optional solvents, polyols, and t-alkyl hydroperoxides are listed above. Non-limiting examples of suitable t-alkylperoxy haloformates of Structure L include t-butylperoxy chloroformate, t-amylperoxy chloroformate, 2-methyl-2-pentylperoxy chloroformate, 3-methyl-3-pentylperoxy chloroformate and 3-methyl-1-butyn-3-ylperoxy chloroformate.

Novel peroxide-substituted bis(monoperoxycarbonates) of Structure A, where $R^1$ is selected from 1,1,4-trimethyl-4(t-butylperoxy)pentyl radical and 1,1,4-trimethyl-4(t-amylperoxy)pentyl radical, and where n is 2, can be prepared by reacting a hydroperoxide, selected from 1,1,4-trimethyl-4(t-butylperoxy)pentyl hydroperoxide and 1,1,4-trimethyl-4(t-amylperoxy)pentyl hydroperoxide, with a bis(haloformate) of Structure C (where n=2), at –30° C. to 50° C., optionally in the presence of an inorganic or organic base, and optionally in the presence of one or more solvents.

Non-limiting examples of suitable bis(haloformates) of Structure C (where n=2), that can be reacted with 1,1,4-trimethyl-4(t-butylperoxy)pentyl hydroperoxide or 1,1,4-trimethyl-4(t-amylperoxy)pentyl hydroperoxide, include 1,2-bis(chlorocarbonyloxy)ethane, 1,2- and 1,3-bis(chlorocarbonyloxy)propanes, 2,2-dimethyl-1,3-bis(chlorocarbonyloxy)propane, 1,6-bis(chlorocarbonyloxy)hexane, 1,5-bis(chlorocarbonyloxy)-3-oxapentane, 1,4-bis(chlorocarbonyloxy)-2-butene and bis(monoperoxycarbonates) of Structures HH and II,

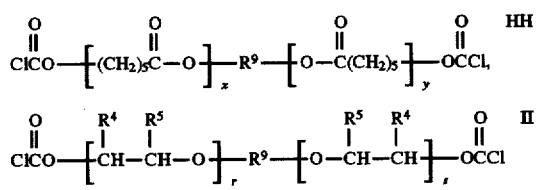

The above bis(haloformates) can be prepared by reacting 0% to 100% excess carbonyl dihalides (such as the dibromide or the dichloride, i.e., phosgene) with the corresponding diol in the presence or absence of a tetraalkylurea (e.g., tetramethylurea) and in the presence or absence of a solvent, until the reaction is completed. The excess carbonyl dibromide or phosgene is removed by stripping or by distillation.

Non-limiting examples of suitable diols that react with carbonyl dihalides to form the bis(haloformates) of Structure C (where n=2) include 1,2-ethanediol, 1,2- and 1,3-propanediols, 1,2-, 1,3- and 1,4-butanediols, 2-butene-1,4-diol, 2-ethyl-1,3-hexanediol, 2,2,4-trimethyl-1,3-pentanediol, 1,6-hexanediol, diethylene glycol, dipropylene glycol, and polycaprolactone diols of Structure JJ (TONE®

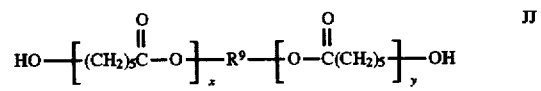

diols, such as TONE® 200 and TONE® 210; manufactured by Union Carbide Corporation) and polyalkylene glycols of Structure KK,

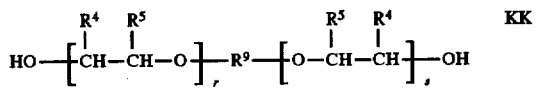

Novel Poly(monoperoxycarbonate) Compositions of Structure A—Illustrative Examples Non-limiting examples of the novel poly(monoperoxycarbonate) compositions of Structure A, in addition to those in the working examples, include the following:

1,1,1-tris(t-amylperoxycarbonyloxymethyl)ethane, 1,1,1-tris(t-amyl-peroxycarbonyloxymethyl)propane, 1,1,1-tris(t-amylperoxycarbonyl-oxymethyl)butane, 1,1-bis[2-(t-amylperoxycarbonyloxy)ethoxymethyl]-1-[2-(t-butylperoxycarbonyloxy)ethoxymethyl)propane, 1-[2-(t-amylperoxycarbonyloxy)ethoxymethyl]-1,1-bis[2-(t-butylperoxycarbonyloxy)ethoxymethyl]propane, 1,2,3-tris(t-amylperoxy-carbonyloxy)propane, 1,2,3-tris(t-butylperoxycarbonyloxy)hexane, 1,2,3-tris(t-butylperoxycarbonyloxy)heptane, 1,2,4-tris(t-butylperoxycarbonyloxy)butane, 1,2,6-tris(t- butylperoxycarbonyloxy)hexane, 1,3,5-tris(t-butylperoxycarbonyloxy)cyclohexane, tetrakis-(t-amylperoxycarbonyloxymethyl)methane, 1,2,3,4-tetrakis (t-amyl-peroxycarbonyloxy)butane, 1,1,1,5,5,5-hexa(t-butylperoxycarbonyl-oxymethyl)-3-oxapentane, 1,5-bis [1,1,4-trimethyl-4(t-amylperoxy) pentylperoxycarbonyloxy]-3-oxapentane, 1,1,1-tris[1,1,4-trimethyl-4(t-butylperoxy) pentylperoxycarbonyloxymethyl]propane, 1,1,1,5,5,9,9, 9-octa(t-butylperoxycarbon-yloxymethyl)-3,7-dioxanonane, and the tris- and tetrakis(t-alkyl monoperoxycarbonates) of polycaprolactone triols and tetraols and polyether triols and tetraols, i.e., compositions of Structures M, N, O and P, respectively:

ciency (reduced initiator requirements, etc.). Ethylenically unsaturated monomers include olefins, such as ethylene, propylene, styrene, alpha-methylstyrene, p-methylstyrene, chlorostyrenes, bromo-styrenes, vinylbenzyl chloride, vinylpyridine and divinylbenzene; diolefins, such as 1,3-butadiene, isoprene and chloroprene; vinyl esters, such as vinyl acetate, vinyl propionate, vinyl laurate, vinyl benzoate and divinyl carbonate; unsaturated nitriles, such as acrylonitrile and methacrylonitrile; acrylic acid and methacrylic acid and their anhydrides, esters and amides, such as acrylic acid anhydride, allyl, methyl, ethyl, n-butyl, 2-hydroxyethyl, glycidyl, lauryl and 2-ethylhexyl acrylates and methacrylates, and acrylamide and methacrylamide; maleic anhydride and itaconic anhydride; maleic, itaconic and

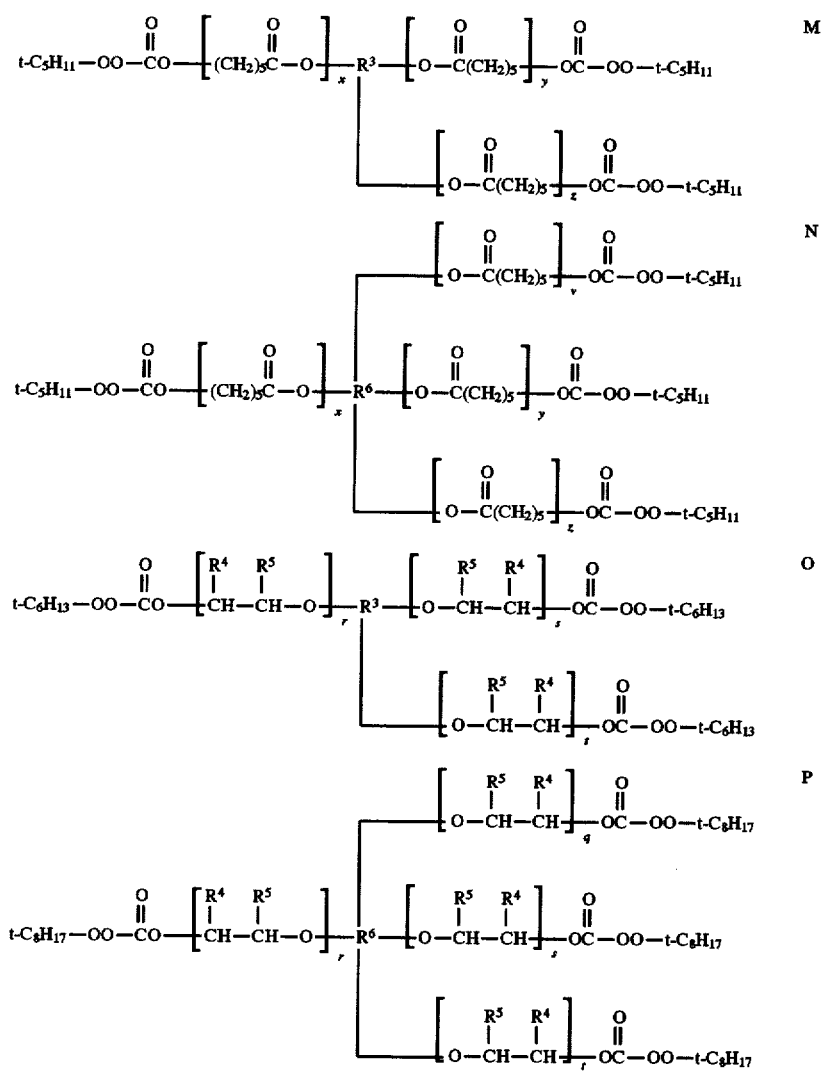

where t-$C_5H_{11}$ is t-amyl, t-$C_6H_{13}$ is 2-methyl-2-pentyl or 3-methyl-3-pentyl and t-$C_8H_{17}$- is 2-methyl-2-heptyl or 1,1,3,3-tetramethylbutyl.

Novel Poly(monoperoxycarbonate) Compositions of Structure A—Utility

A. Polymerization of Ethylenically Unsaturated Monomers

In the free-radical polymerizations of ethylenically unsaturated monomers at suitable temperatures and pressures the novel peroxide compositions of Structure A of this invention were found to be effective initiators with respect to effifumaric acids and their esters; vinyl halo and vinylidene dihalo compounds, such as vinyl chloride, vinyl bromide, vinyl fluoride, vinylidene chloride and vinylidene fluoride; perhalo olefins, such as tetrafluoro-ethylene, hexafluoropropylene and chlorotrifluoroethylene; vinyl ethers, such as methyl vinyl ether, ethyl vinyl ether and n-butyl vinyl ether; allyl esters, such as allyl acetate, allyl benzoate, allyl ethyl carbonate, triallyl phosphate, diallyl phthalate, diallyl fumarate, diallyl glutarate, diallyl adipate, diallyl carbonate, diethylene glycol bis(allyl carbonate) (i.e., ADC); acrolein; methyl vinyl ketone; or mixtures thereof.

In the free-radical graft polymerization of ethylenically unsaturated monomers onto polymers at suitable temperatures and pressures the novel peroxide compositions of Structure A of this invention are also effective initiators with respect to grafting efficiency. Ethylenically unsaturated monomers include: styrene monomers such as styrene, alpha-methylstyrene, p-methylstyrene, chlorostyrenes, bromostyrenes and vinylbenzyl chloride; unsaturated nitriles, such as acrylonitrile and methacrylonitrile; acrylic acid and methacrylic acid esters, such as allyl, methyl, ethyl, n-butyl, 2-hydroxyethyl, glycidyl, lauryl and 2-ethylhexyl acrylates and methacrylates; and maleic anhydride. Graftable polymers include polybutadiene and polyisoprene. Two important polymeric compositions that are prepared by grafting of ethylenically unsaturated monomers onto polymers backbones are high-impact polystyrene (HIPS) and acrylonitrile-butadiene-styrene (ABS). HIPS is produced by the free-radical grafting of styrene onto polybutadiene whereas ABS is produced by the free-radical grafting of acrylonitrile and styrene onto polybutadiene. Such polybutadiene-modified compositions have impact resistances that are superior to the unmodified polymers.

Temperatures of 0° C. to 190° C., preferably 20° C. to 175° C., more preferably 30° C. to 160° C. and levels of tris- and poly(monoperoxycarbonates) of Structure A (on a pure basis) of 0.002 to 10% or more, preferably 0.0050% to 2%, more preferably 0.01% to 1% by weight based on monomer, are normally employed in conventional polymerizations and copolymerizations of ethylenically unsaturated monomers, and in grafting of ethylenically unsaturated monomers onto polymer backbones. The novel peroxide compositions of this invention can be used in combination with other free-radical initiators such as 1,5-di(t-butylperoxycarbonyloxy)-3-oxapentane, 2,5-dimethyl-2,5-di-(2-ethylhexanoylperoxy) hexane, 2,5-dimethyl-2,5-di(isopropoxycarbonylperoxy) hexane, 2,5-dimethyl-2-(2-ethylhexoxycarbonylperoxy)-5-(t-butylperoxy)hexane, t-butyl peroxybenzoate, t-amyl peroxybenzoate, di-t-butyl diperoxyphthalate and some of those listed at the bottom of column 4 and the top of column 5 of U.S. Pat. No. 4,525,308 (to Pennwalt Corporation, Jun. 25, 1985). Using the peroxide compositions of this invention in combination with these initiators adds flexibility to the processes of polymer producers and allows them to "fine tune" their polymerization processes.

B. Curing of Unsaturated Polyester Resins

In the curing of unsaturated resin compositions by heating at suitable curing temperatures in the presence of free-radical curing agents, the novel poly(monoperoxycarbonate) compositions of Structure A of this invention exhibit enhanced curing activity in the curable unsaturated polyester resin compositions. Unsaturated polyester resins that can be cured by the novel poly(monoperoxycarbonate) compositions of this invention usually include an unsaturated polyester and one or more ethylenically unsaturated monomers.

The unsaturated polyesters are, for instance, polyesters as they are obtained by esterifying at least one ethylenically unsaturated di- or higher polycarboxylic acid, anhydride or acid halide, such as maleic acid, fumaric acid, glutaconic acid, itaconic acid, mesaconic acid, citraconic acid, allylmalonic acid, tetrahydrophthalic acid, and others, with saturated and unsaturated di- or higher polyols, such as ethylene glycol, diethylene glycol, triethylene glycol, 1,2- and 1,3-propanediols, 1,2-, 1,3- and 1,4-butanediols, 2,2-dimethyl-1,3-propanediol, 2-hydroxymethyl-2-methyl-1,3-propanediol, 2-buten-1,4-diol, 2-butyn-1,4-diol, 2,4,4-trimethyl-1,3-pentanediol, glycerol, pentaerythritol, mannitol and others. Mixtures of such di- or higher polyacids and/or mixtures of such di- or higher polyols may also be used. The ethylenically unsaturated di- or higher polycarboxylic acids may be partially replaced by saturated di- or polycarboxylic acids, such as adipic acid, succinic acid, sebacic acid and other, and/or by aromatic di- or higher polycarboxylic acids, such as phthalic acid, trimellitic acid, pyromellitic acid, isophthalic acid and terephthalic acid. The acids used may be substituted by groups such as halogen. Examples of such suitable halogenated acids are, for instance, tetrachlorophthalic acid, tetrabromophthalic acid, 5,6-dicarboxy-1,2,3,4,7,7-hexachlorobicyclo(2.2.1)-2-heptene and others.

The other component of the unsaturated polyester resin composition, the polymerizable monomer or monomers, can preferably be ethylenically unsaturated monomers, such as styrene, alpha-methylstyrene, p-methylstyrene, chlorostyrenes, bromostyrenes, vinylbenzyl chloride, divinylbenzene, diallyl maleate, dibutyl fumarate, triallyl phosphate, triallyl cyanurate, diallyl phthalate, diallyl fumarate, methyl acrylate, methyl methacrylate, n-butyl acrylate, n-butyl methacrylate, ethyl acrylate, and others, or mixtures thereof, which are known in the art as copolymerizable with said unsaturated polyesters. A preferred unsaturated polyester resin composition contains as the unsaturated polyester component the esterification product of 1,2-propanediol (a polyol), maleic anhydride (an anhydride of an unsaturated polycarboxylic acid) and phthalic anhydride (an anhydride of an aromatic dicarboxylic acid) as well as the monomer component, styrene.

Other types of unsaturated polyester resin compositions can be cured using the novel peroxide compositions of this invention as curing catalysts. These resins, called unsaturated vinyl ester resins, consist of a vinyl ester resin portion and one or more polymerizable monomer components. The vinyl ester resin component can be made by reacting a chloroepoxide, such as epichlorohydrin, with appropriate amounts of a bisphenol such as Bisphenol A (i.e., 2,2-(4-hydroxyphenyl)propane), in the presence of a base, such as sodium hydroxide, to yield a condensation product having terminal epoxy groups derived from the chloroepoxide. Subsequent reaction of the condensation product with polymerizable unsaturated carboxylic acids, such as acrylic acid and methacrylic acid, in the presence or absence of acidic or basic catalysts, results in formation of the vinyl ester resin component. Normally, styrene is added as the polymerizable monomer component to complete the preparation of the unsaturated vinyl ester resin composition.

Temperatures of about 20° C. to 200° C. and levels of novel poly(monoperoxycarbonates) of Structure A of about 0.05% to 5% or more, preferably 0.10% to 4%, more preferably 0.25% to 3% by weight of curable unsaturated polyester resin composition are normally employed.

The unsaturated polyester resin compositions described above can be filled with various materials, such as sulfur, glass, carbon and boron fibers, carbon blacks, silicas, metal silicates, clays, metal carbonates, antioxidants (AO's), heat, ultraviolet (UV) and light stabilizers, sensitizers, dyes, pigments, accelerators, metal oxides, such as zinc oxide, blowing agents, nucleating agents and others.

C. Curing of Allyl Diglycol Carbonate (ADC) Resins

In the curing or polymerizing of diethylene glycol bis (allyl carbonate (ADC),

by heating ADC monomer at suitable curing temperatures in the presence of free-radical curing agents, the novel poly (monoperoxycarbonate) compositions of Structure A of this invention exhibit enhanced curing or polymerizing activity for ADC monomer compositions. ADC was introduced commercially as CR-39 monomer (CAS Reg. No. 142-22-3) by Pittsburgh Plate Glass Company (PPG) and is produced by reacting diethylene glycol bis(chloroformate) with allyl alcohol in the presence of alkali (R. Dowbenko, in J. I. Kroschwitz and M. Howe-Grant, eds., Kirk— Othmer— Encyclopedia of Chemical Technology, "Allyl Monomers and Polymers," Fourth Edition, Vol. 2, Wiley-Interscience Publication, John Wiley & Sons, Inc., New York, 1992, pp 163–168). The ADC monomer can be cured or polymerized alone or with other co-monomers such as acrylic acid esters, methacrylic acid esters, allyl esters, diallyl dicarboxylates (e.g., diallyl phthalate), maleic anhydride and other monomers to produce clear castings or lenses that are transparent, tough, break-resistant and solvent-resistant. Curing or polymerizing of ADC monomer compositions are carried out in bulk (no solvent present). In general, curing or polymerizing of ADC monomer compositions to form cast sheets or lenses is carried out in two stages. The first stage involves the major part of the polymerization and occurs in the presence of the curing initiator at temperatures of 35° C. to 150° C. Curing or polymerization times of the first stage vary from about 5 hours to 50 hours. The second stage of the curing or polymerizing of ADC monomer compositions involves post-curing or annealing of the ADC resin for one to several hours at 100° C. to 170° C.

Levels of the novel poly(monoperoxycarbonate) compositions of Structure A about 1% to 6% or more, preferably 2% to 5%, more preferably 2.5% to 4% by weight of curable or polymerizable ADC monomer composition, are normally employed.

The ADC resin compositions described above can be filled with various materials, such as antioxidants (AO's), heat, ultraviolet (UV) and light stabilizers, tints, photochromic additives and dyes. In addition, the ADC resin compositions can contain additives such as acrylic polymers and the anti-shrink, low molecular weight acrylic resins disclosed in U.S. Pat. No. 4,217,433 (to Pennwalt Corporation, Aug. 12, 1980). Such anti-shrink additives are employed to counter shrinkage that occurs when ADC monomer is polymerized.

D. Curing of Elastomers and Crosslinking of Thermoplastic Polymers

In the curing of elastomeric compositions, and the crosslinking of polymer compositions, by heating at suitable curing and crosslinking temperatures in the presence of free-radical curing and crosslinking agents, the novel and poly(monoperoxycarbonate) compositions of Structure A of this invention exhibit curing and crosslinking activities.

Elastomeric resin compositions that can be cured by the novel poly(monoperoxycarbonate) compositions of this invention include elastomers such as ethylene-propylene copolymers (EPR), ethylene-propylene-diene terpolymers (EPDM), polybutadiene (PBD), silicone rubber (SR), nitrile rubber (NR), neoprene, fluoroelastomers and ethylene-vinyl acetate copolymer (EVA).

Polymer compositions that can be cross-linked by the novel poly(monoperoxycarbonate) compositions of this invention include olefin thermoplastics such as chlorinated polyethylene (CPE), low density polyethylene (LDPE), linear-low density polyethylene (LLDPE), and high density polyethylene (HDPE). Other cross-linkable thermoplastic polymers include polyvinyl chloride (PVC), polystyrene, poly(vinyl acetate), polyacrylics, polyesters, polycarbonate, etc.

Temperatures of about 80° C. to 310° C. and poly (monoperoxycarbonate) levels of about 0.1% to 10%, preferably 0.5% to 5%, more preferably 0.5% to 3% based on weight of curable elastomeric resin composition or crosslinkable olefin polymer composition, are normally employed.

The curable elastomeric resin composition or crosslinkable polymer composition can be optionally filled with the materials listed above for use with the conventional unsaturated polyester resin compositions.

E. Modification of Polyolefins and Other Polymers

In the processes for modifying polyolefins (e.g., beneficial degradation of polypropylene (PP) by reducing the polymer molecular weight and reducing the polymer molecular weight distribution of PP and enhancing the molecular weight and film forming properties of linear low density polyethylene (LLDPE)) and copolymers, the novel poly (monoperoxycarbonate) compositions of Structure A of this invention exhibit polyolefin modification activity. Other polymers that can be modified with tris- and poly (monoperoxy-carbonates) include high density PE (HDPE), ethylene-propylene copolymer, etc.

Temperatures of about 140° C. to 340° C. and tris- and poly(monoperoxycarbonate) levels of about 0.001% to 1.0%, preferably 0.01% to 1.0%, more preferably 0.01% to 0.5% based on weight of modifiable polyolefins or copolymers are normally employed. Optionally, up to 1% by weight of molecular oxygen can be employed as a modification co-catalyst.

Novel Poly(monoperoxycarbonate) Compositions of Structure A—Preparative and Utility Examples The following examples further illustrate the best methods contemplated for practicing the instant invention, and are presented to provide detailed preparative and utility illustrations of the invention and are not intended to limit the breadth and scope of the invention.

EXAMPLE 1

Preparation of 1,1,1-Tris(t-butylperoxycarbonyloxymethyl)ethane, (I-1)

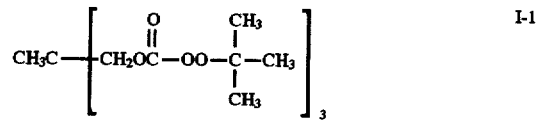

In this example the product was prepared in two synthetic steps. In the first step 1,1,1-tris(hydroxymethyl)ethane (0.15 mole) was reacted with excess phosgene (0.85 mole) in 175 mL of 1,4-dioxane at 0°–8° C. 1,1,3,3-Tetramethylurea (0.4 g) was added to suppress cyclic carbonate formation. Upon completion of the reaction, the excess phosgene and the solvent were stripped from the product at 15°–30° C. and reduced pressure to produce 1,1,1-tris (chlorocarbonyloxymethyl)ethane, a liquid, having an assay of 89.3% and in a corrected yield of 74.6%.

In the second step, 1,1,1-tris(chlorocarbonyloxymethyl) ethane was reacted with t-butyl hydroperoxide, in the presence of aqueous potassium hydroxide and a surfactant, to yield the product as described below:

A 300 mL water-jacketed reactor, equipped with a mechanical stirrer, a thermometer and an addition funnel, was charged with 70.0 g (0.25 mole) of 20% aqueous potassium hydroxide solution, 25 g (0.25 mole) of 90.2% t-butyl hydroperoxide and 10 drops of TERGITOL® NP-10 [a surfactant mixture containing poly(oxy-1,2-ethanediyl), α-(4-nonylphenyl)-ω-hydroxy-; CAS registry No., 26027-38-3, and poly(oxy-1,2-ethanediyl), α-hydro-ω-hydroxy-; CAS registry No., 25322-68-3; manufactured by Union Carbide] and the resulting solution was stirred at 25° C. for 10 minutes. To the stirred mixture at 22°–29° C. was slowly added 17.2 g (0.05 mole) of 89.3% 1,1,1-tris (chlorocarbonyloxymethyl)ethane over a period of 25 minutes. After the addition was completed the reaction mass was stirred for 3 hours at 30°–35° C. after which 150 mL MTBE was added and the reaction mass was stirred one minute at 30°–35° C. The lower aqueous layer was then separated and the organic layer was cooled to 17° C. and was washed with 100 mL of aqueous 10% potassium hydroxide. The organic layer was then washed three times with 50 mL portions of aqueous 10% sodium hydrogen sulfite solution, then with 100 mL of 10% aqueous sodium hydroxide solution, and then with saturated aqueous sodium sulfate solution to a pH of 7–8. The product solution was dried over 5% by weight of anhydrous MgSO$_4$, and, after separation of the spent desiccant by filtration, the solvent was removed in vacuo leaving 7.4 g (31.6% of theory, uncorrected) of white solid, mp=55°–60° C. An infra red (IR) spectrum of the product showed a major monoperoxycarbonate carbonyl band at 1790 cm$^{-1}$ and a major carbonate carbonyl band at about 1755 cm$^{-1}$. There was no OH band in the IR spectrum. The product contained 9.42% active oxygen (theory, 10.25%) according to a peroxyester active oxygen method, therefore, the assay of the product was 91.9% and the corrected yield was 29.1%.

Based on the method of preparation, yield data, and IR spectral data the product obtained in this reaction was the desired title product.

EXAMPLE 2

Preparation of 1,1,1-Tris(t-butylperoxycarbonyloxymethyl)propane, (I-2)

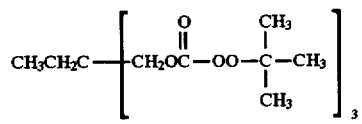

1,1,1-tris(chlorocarbonyloxymethyl)propane, a liquid, having an assay of 87.7% and in a corrected yield of 95.6%.

In the second step, 1,1,1-tris(chlorocarbonyloxymethyl) propane was reacted with t-butyl hydroperoxide, in the presence of aqueous potassium hydroxide and a surfactant, to yield the product as described below:

A 300 mL water-jacketed reactor, equipped with a mechanical stirrer, a thermometer and an addition funnel, was charged with 56.0 g (0.20 mole) of 20% aqueous potassium hydroxide solution and 19.5 g (0.20 mole) of 92% t-butyl hydroperoxide and the resulting solution was stirred at about 25° C. To the stirred mixture at 23°–31° C. was slowly added a solution of 18.3 g (0.05 mole) of 87.7% 1,1,1-tris(chlorocarbonyloxymethyl)propane and 50 mL of MTBE over a period of 30 minutes. After the addition was completed the reaction mass was stirred for 3 hours at 30°–32° C. after which 50 mL MTBE was added and the reaction mass was stirred one minute at 30°–32° C. The lower aqueous layer was then separated and the organic layer was cooled to 12° C. and was washed with 50 mL of aqueous 10% sodium hydrogen sulfite solution. The resulting organic layer was then washed twice with 50 mL portions of 3% aqueous sodium hydrogen carbonate solution. The product solution was dried over 5% by weight of anhydrous MgSO$_4$, and, after separation of the spent desiccant by filtration, the solvent was removed in vacuo leaving 10.8 g (44.8% of theory, uncorrected) of a clear, colorless liquid. An IR spectrum of the product showed a major monoperoxycarbonate carbonyl band at 1792 cm$^{-1}$ and a major carbonate carbonyl band at about 1767 cm$^{-1}$. There was only a trace of an OH band in the IR spectrum. The product contained 8.65% active oxygen (theory, 9.95%) according to a peroxyester active oxygen method, therefore, the assay of the product was 86.9% and the corrected yield was 38.9%.

Based on the method of preparation, yield data, and IR spectral data the product obtained in this reaction was the desired title product.

EXAMPLE 3

Preparation of Polycaprolactone Tris(mono-t-butylperoxycarbonate), I-3

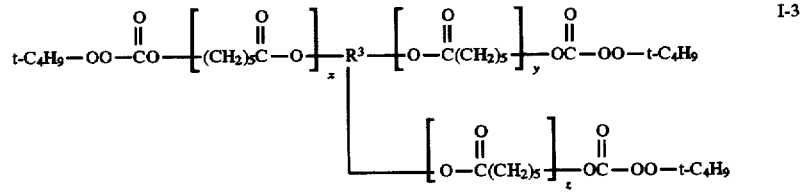

In this example the product was prepared in two synthetic steps. In the first step 1,1,1-tris(hydroxymethyl)propane (0.10 mole) was reacted with excess phosgene (0.60 mole) in 200 mL of 1,4-dioxane at 2°–8° C. 1,1,3,3-Tetramethylurea (0.3 g) was added to suppress cyclic carbonate formation. Upon completion of the reaction, the excess phosgene and the solvent were stripped from the product at 20°–30° C. and reduced pressure to produce (where the sum of x, y and z is about 2 and R$^3$ is a triradical)

In this example the product was prepared in two synthetic steps. In the first step 0.12 mole of a polycaprolactone triol (C-1), (TONE® 0301; molecular weight=300; manufactured by Union

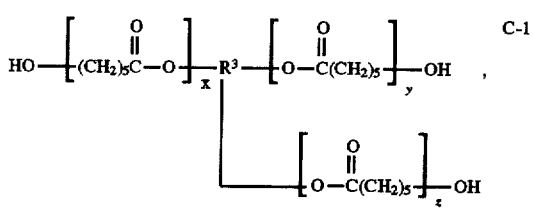

(where the sum of x, y and z is about 2 and $R^3$ is a triradical) Carbide Corp.), was reacted with excess phosgene (0.60 mole) at 5°–10° C. Upon completion of the reaction, the excess phosgene was stripped from the product at 15°–25° C. and reduced pressure to produce a polycaprolactone tris(chloroformate), a light pink viscous liquid, having an assay of 91.0% and in a corrected yield of 84.2%.

In the second step, the polycaprolactone tris (chloroformate) was reacted with t-butyl hydroperoxide, in the presence of aqueous potassium hydroxide, to yield the product as described below:

A 250 ml water-jacketed reactor, equipped with a mechanical stirrer, a thermometer and an addition funnel, was charged with 28.0 g (0.10 mole) of 20% aqueous potassium hydroxide solution, 12.9 g (0.10 mole) of aqueous 70% t-butyl hydroperoxide and 3 drops (ca. 0.1 g) of TERGITOL® NP-10 at 20°–30° C. The resulting solution was stirred at about 25° C. To the stirred solution at 23°–29° C. was slowly added 16.1 g (0.03 mole) of 91.0% polycaprolactone tris(chloroformate) over a period of 20 minutes. About 50 mL of MTBE was added in order to maintain good stirring. After the addition was completed the reaction mass was stirred for 3 hours at 30° C. during which more MTBE (50–60 mL) was added. The reaction mass was then allowed to separate into liquid phases. The lower aqueous layer was then separated and the remaining organic layer was cooled to 15° C. and was washed with 50 mL of aqueous 10% sodium hydrogen sulfite solution, then washed with 50 mL of aqueous 10% potassium hydroxide solution and with 50 mL portions of saturated aqueous sodium sulfate solution until the pH was 7–8. The product solution was dried over 5% by weight of anhydrous $MgSO_4$, and, after separation of the spent desiccant by filtration, the solvent was removed in vacuo leaving 19.6 g (ca. 100% of theory, uncorrected) of a colorless liquid. An IR spectrum of the product showed a major monoperoxycarbonate carbonyl band at 1785 $cm^{-1}$ and a major carbonate or ester carbonyl band at about 1740 $cm^{-1}$. There was no OH band in the IR spectrum. The product contained 6.69% active oxygen (theory, 7.40%) according to a peroxyester active oxygen method, therefore, the assay of the product was 90.4% and the corrected yield was 91.3%.

Based on the method of preparation, yield data, and IR spectral data the product obtained in this reaction was the desired title product.

EXAMPLE 4

Preparation of Polycaprolactone Tris(mono-t-butylperoxycarbonate), I-4

In this example the product was prepared in two synthetic steps. In the first step 0.05 mole of a polycaprolactone triol (C-2), (TONE® 0305; molecular weight=540; manufactured by Union

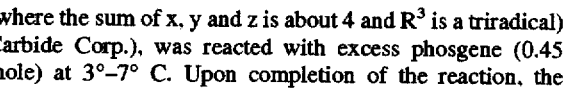

(where the sum of x, y and z is about 4 and $R^3$ is a triradical) Carbide Corp.), was reacted with excess phosgene (0.45 mole) at 3°–7° C. Upon completion of the reaction, the excess phosgene was stripped from the product at 15°–25° C. and reduced pressure to produce a polycaprolactone tris(chloroformate), a light pink liquid, having an assay of 97.9% and in a corrected yield of 93.3%.

In the second step, the polycaprolactone tris (chloroformate) was reacted with t-butyl hydroperoxide, in the presence of aqueous potassium hydroxide, to yield the product as described below:

A 200 mL water-jacketed reactor, equipped with a mechanical stirrer, a thermometer and an addition funnel, was charged with 15.7 g (0.07 mole) of 25% aqueous potassium hydroxide solution and 9.0 g (0.07 mole) of aqueous 70% t-butyl hydroperoxide. The resulting solution was stirred at about 25° C. To the stirred solution at 24°–28° C. was slowly added 14.8 g (0.02 mole) of 97.9% polycaprolactone tris(chloroformate) over a period of 15 minutes.

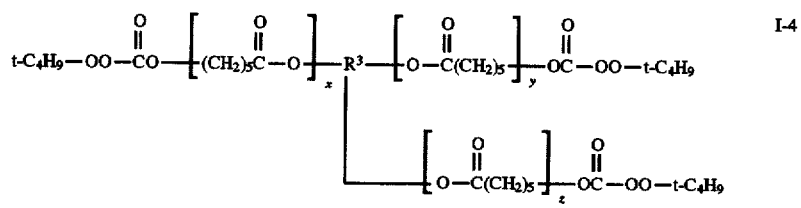

(where the sum of x, y and z is about 4 and $R^3$ is a triradical)

After the addition was completed the reaction mass was stirred for 3.5 hours at 28°–32° C. after which 80 mL MTBE was added and the reaction mass was stirred one minute at 28°–32° C., then allowed to separate. The lower aqueous layer was then separated and the organic layer was cooled to 15° C. and was washed with 25 mL of aqueous 10% sodium hydrogen sulfite solution. The resulting organic layer was then washed with 25 mL of aqueous 10% potassium hydroxide solution and with 50 mL portions of saturated aqueous sodium sulfate solution until the pH was 7–8. The product solution was dried over 5% by weight of anhydrous $MgSO_4$, and, after separation of the spent desiccant by filtration, the solvent was removed in vacuo leaving 17.4 g (98% of theory, uncorrected) of a colorless liquid. An IR spectrum of the product showed a major monoperoxycarbonate carbonyl band at 1785 $cm^{-1}$ and a major carbonate or ester carbonyl band at about 1730 $cm^{-1}$. There was only a trace of an OH band in the IR spectrum. The product contained 5.00 % active oxygen (theory, 5.40%) according to a peroxyester active oxygen method, therefore, the assay of the product was 92.6% and the corrected yield was 90.7%.

Based on the method of preparation, yield data, and IR spectral data the product obtained in this reaction was the desired title product.

EXAMPLE 5

Preparation of the 1,1,1-Tris[2-(t-butylperoxycarbonyloxy)ethoxymethyl]propane, I-5

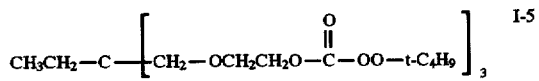

In this example, the product (i.e., 1,1,1-tris[2-(t-butyl-peroxycarbonyloxy)ethoxymethyl]propane, I-5) was prepared in two synthetic steps. In the first step 0.15 mole of a polyether triol (i.e., 1,1,1-tris[2-hydroxyethoxymethyl]propane, C-3), a commercial triol product (VORANOL® 234–630; molecular weight=267;

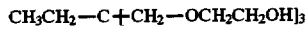

produced by Dow Chemical), was reacted with excess phosgene (0.65 mole) at 3°–7° C. The reaction mixture was then stirred for 4 hours at 0°–10° C. and allowed to stand overnight at 20°–25° C. The excess phosgene was then stripped from the product at 20°–25° C. and at reduced pressure for 5 hours to produce a polyether tris (chloroformate), a clear, viscous liquid, having an assay of 97.4% and in a corrected yield of 94.8%.

In the second step, the polyether tris(chloroformate) was reacted with t-butyl hydroperoxide, in the presence of aqueous potassium hydroxide, to yield the product as described below:

A 200 ml water-jacketed reactor, equipped with a mechanical stirrer, a thermometer and an addition funnel, was charged with 29.4 g (0.105 mole) of 20% aqueous potassium hydroxide solution, 13.5 g (0.105 mole) of aqueous 70% t-butyl hydroperoxide and 3 drops (ca. 0.1 g) of TERGITOL® NP-10 at 20°–30° C. The resulting solution was stirred at about 25° C. To the stirred solution at 23°–29° C. was slowly added a solution consisting of 14.0 g (0.03 mole) of 97.4% polyether tris(chloroformate) and 20 ml of MTBE over a period of 15 minutes. After the addition was completed the reaction mass was stirred for 2.5 hours at 30° C. after which 80–90 ml MTBE was added and the reaction mass was stirred one minute at 30° C., then allowed to separate into liquid phases. The lower aqueous layer was then separated and discarded. The organic layer was cooled to 15° C. and was washed with 50 ml of aqueous 10% potassium hydroxide solution. The crude product solution was then washed with 50 ml of aqueous 10% sodium hydrogen sulfite solution. The resulting organic layer was then washed with 50 ml of saturated aqueous potassium hydrogen carbonate solution. The organic solution was then washed with 50 ml of saturated aqueous sodium sulfate solution to a pH of about 7. The product solution was dried over 5% by weight of anhydrous $MgSO_4$, and, after separation of the spent desiccant by filtration, the solvent was removed in vacuo leaving 18.3 g (ca. 100% of theory, uncorrected) of a colorless liquid product. An IR spectrum of the product showed a major monoperoxycarbonate carbonyl band at 1785 $cm^{-1}$ and a major carbonate band at about 1735 $cm^{-1}$. There was no OH band in the IR spectrum. The product contained 7.52% active oxygen (theory, 7.81%) according to a peroxyester active oxygen method, therefore, the assay of the product was 94.2% and the corrected yield was 93.7%.

Based on the method of preparation, yield data, and IR spectral data the product obtained in this reaction was the desired title product.

EXAMPLE 6

Preparation of Polycaprolactone Tetrakis(mono-t-butylperoxycarbonate), I-6

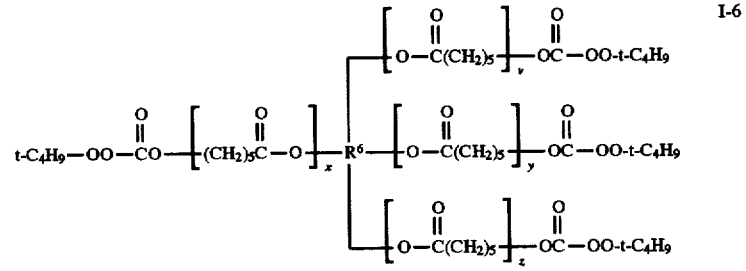

(where the sum of v, x, y and z is about 8 and $R^6$ is a tetraradical)

In this example the product was prepared in two synthetic steps. In the first step 0.03 mole of a polycaprolactone tetraol (C-4), an experimental caprolactone oligomeric tetraol (TONE® 4411;

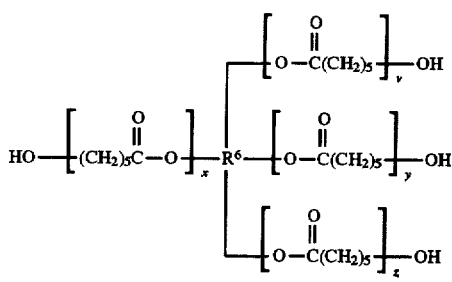

C-4

(where the sum of v, x, y and z is about 8 and $R^6$ is a tetraradical)
molecular weight=1006; produced by Union Carbide Corp.), was reacted with excess phosgene (0.35 mole) at 3°–7° C. The reaction mixture was then stirred for 5 hours at 10°–20° C. and allowed to stand overnight at 20°–25° C. The excess phosgene was then stripped from the product at 20°–25° C. and at reduced pressure for 5 hours to produce a polycaprolactone tetrakis(chloroformate), a clear, viscous liquid, having an assay of 97.3% and in a corrected yield of 91.9%.

In the second step, the polycaprolactone tetrakis (chloroformate) was reacted with t-butyl hydroperoxide, in the presence of aqueous potassium hydroxide, to yield the product as described below:

A 200 ml water-jacketed reactor, equipped with a mechanical stirrer, a thermometer and an addition funnel, was charged with 11.2 g (0.05 mole) of 25% aqueous potassium hydroxide solution and 6.4 g (0.05 mole) of aqueous 70% t-butyl hydroperoxide at 20°–30° C. The resulting solution was stirred at about 25° C. To the stirred solution at 24°–31° C. was slowly added a solution consisting of 12.9 g (0.01 mole) of 97.3% polycaprolactone tetrakis (chloroformate) and 30 ml of MTBE over a period of 15 minutes. After the addition was completed the reaction mass was stirred for 3 hours at 30°–35° C. after which 70 ml MTBE was added and the reaction mass was stirred one minute at 30°–35° C., then allowed to separate. The lower aqueous layer was then separated and the organic layer was cooled to 15° C. and was washed with 50 ml of aqueous 10% potassium hydroxide solution. The crude product solution was then washed with 50 mL of aqueous 10% sodium hydrogen sulfite solution. The resulting organic layer was then washed with aqueous 10% potassium hydrogen carbonate solution to a pH of about 7. The product solution was dried over 5% by weight of anhydrous $MgSO_4$, and, after separation of the spent desiccant by filtration, the solvent was removed in vacuo leaving 14.9 g (ca. 100% of theory, uncorrected) of a viscous, colorless liquid. An IR spectrum of the product showed a major monoperoxycarbonate carbonyl band at 1785 $cm^{-1}$ and a major carbonate or ester carbonyl band at about 1730 $cm^{-1}$ There was no OH band in the IR spectrum. The product contained 3.73% active oxygen (theory, 4.35%) according to a peroxyester active oxygen method, therefore, the assay of the product was 85.7% and the corrected yield was 86.9%.

Based on the method of preparation, yield data, and IR spectral data the product obtained in this reaction was the desired title product.

EXAMPLE 7

Preparation of Polyether Tetrakis(mono-t-butylperoxycarbonate), I-7

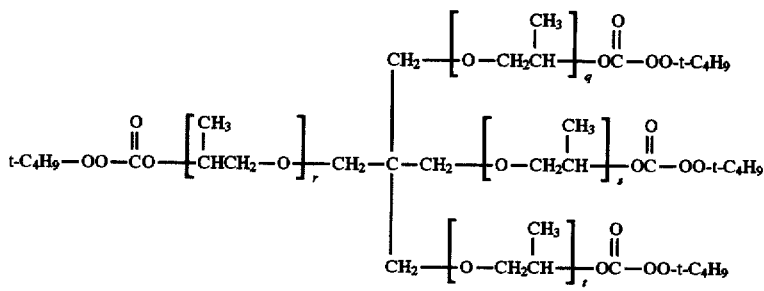

I-7

(Where the sum of q, r, s and t is about 6–7)

In this example the product was prepared in two synthetic steps. In the first step 0.075 mole of polyether tetraol (C-5),

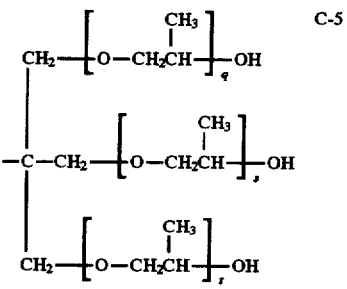

C-5

(Where the sum of q, r, s and t is about 6–7) (PLURACOL® PeP 550; molecular weight=500; manufactured by BASF Corporation), was reacted with excess phosgene (0.60 mole) at 3°–7° C. The reaction mixture was then stirred for 2–3 hours at 10°–20° C. and allowed to stand overnight at 20°–25° C. The excess phosgene was then stripped from the product at 20°–30° C. and at reduced pressure to produce a polyether tetrakis(chloroformate), a clear liquid, having an assay of 100% and in a corrected yield of 97.4%.

In the second step, the polyether tetrakis(chloroformate) was reacted with t-butyl hydroperoxide, in the presence of aqueous potassium hydroxide, to yield the product as described below:

A 250 ml water-jacketed reactor, equipped with a mechanical stirrer, a thermometer and an addition funnel, was charged with 29.2 g (0.13 mole) of 25% aqueous potassium hydroxide solution and 16.7 g (0.13 mole) of aqueous 70% t-butyl hydroperoxide at 22°–29° C. The resulting solution was stirred at about 25° C. To the stirred solution at 23°–28° C. was slowly added 18.8 g (0.025 mole) of 100% polyether tetrakis(chloroformate) over a period of 15 minutes. After the addition was completed the reaction mass was stirred for 3 hours at 25°–30° C. after which 100 ml MTBE was added and the reaction mass was stirred one minute at about 30° C., then allowed to separate into liquid phases. The lower aqueous layer was then separated and the remaining organic layer was cooled to 12° C. and was washed with 50 ml of aqueous 10% sodium hydrogen sulfite solution, then washed with 50 ml of aqueous 10% potassium hydroxide solution and with 50 ml portions of saturated aqueous sodium sulfate solution until the pH was 7–8. The product solution was dried over 5% by weight of anhydrous MgSO$_4$, and, after separation of the spent desiccant by filtration, the solvent was removed in vacuo leaving 22.4 g (92.9% of theory, uncorrected) of a colorless liquid. An IR spectrum of the product showed a major monoperoxycarbonate carbonyl band at 1785 cm$^{-1}$ and a major carbonate or ester carbonyl band at about 1752 cm$^{-1}$. There was only a trace of an OH band in the IR spectrum. The product contained 6.16% active oxygen (theory, 6.64%) according to a peroxyester active oxygen method, therefore, the assay of the product was 92.8% and the corrected yield was 86.3%.

Based on the method of preparation, yield data, and IR spectral data the product obtained in this reaction was the desired title product.

EXAMPLE 8

Preparation of a Polycaprolactone Bis(mono-t-butylperoxycarbonate), A-1

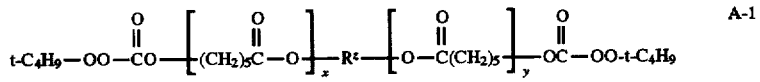

(where the sum of x and y is about 4 and R$^z$ is a diradical)

In this example the product was prepared in two synthetic steps. In the first step 0.03 mole of a polycaprolactone diol (C-6) (TONE® 0200 diol; molecular weight=530; manufactured by

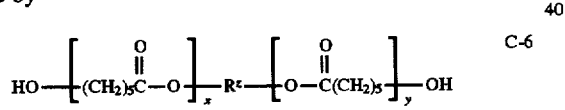

(where the sum of x and y is about 4 and R$^z$ is a diradical) Union Carbide Corp.), was reacted with excess phosgene by the previously-described process. Obtained was polycaprolactone bis(chloroformate), a pink, viscous liquid, having an assay of 100%.

In the second step, the polycaprolactone bis (chloroformate) was reacted with t-butyl hydroperoxide, in the presence of aqueous potassium hydroxide, to yield the product as described below:

A 400 mL water-jacketed reactor, equipped with a mechanical stirrer, a thermometer and an addition funnel, was charged with 14.9 g (0.12 mole) of 45% aqueous potassium hydroxide solution, 10.0 g of water and 14.1 g (0.11 mole) of aqueous 70% t-butyl hydroperoxide at 20°–30° C. The resulting solution was stirred at about 25° C. To the stirred solution at 23°–31° C. was slowly added 32.7 g (0.05 mole) of 100% polycaprolactone bis(chloroformate) over a period of about 25 minutes. After the addition was completed 75 mL of MTBE was added and the reaction mass was stirred for about 2 hours at 30°±2° C. after which 125 mL of additional MTBE was added and the reaction mass was stirred one minute at 30° C., then allowed to separate into liquid phases. The lower aqueous layer was then separated and discarded. The organic layer was cooled to 15° C. and was washed with 50 mL of aqueous 10% sodium hydrogen sulfite solution at 15°–25° C. Separation of the resulting mass into two liquid phases was very slow. Addition of sodium sulfate enhanced the rate of separation into phases. The lower aqueous phase was removed and discarded. The upper organic solution was then washed twice with 50 mL portions of aqueous 20% potassium hydroxide solution at 20°–30° C. The resulting organic layer was then washed with saturated aqueous sodium sulfate solution to a pH of about 7. The organic product solution was then dried over 5% by weight of anhydrous MgSO$_4$, and, after separation of the spent desiccant by filtration, the solvent was removed in vacuo leaving 33.8 g (ca. 89% of theory, uncorrected) of a viscous, colorless liquid. An IR spectrum of the product showed a major monoperoxycarbonate carbonyl band at 1785 cm$^{-1}$ and a major carbonate or ester carbonyl band at about 1731 cm$^{-1}$. There was no OH band in the IR spectrum. The product contained 3.97% active oxygen (theory, 4.20%) according to a peroxyester active oxygen method, therefore, the assay of the product was 94.5% and the corrected yield was 84.1%.

Based on the method of preparation, yield data, and IR spectral data the product obtained in this reaction was the desired title product.

EXAMPLE 9

Preparation of the 1,1,1-Tris[2-(t-amylperoxycarbonyloxy)ethoxymethyl]propane, I-8

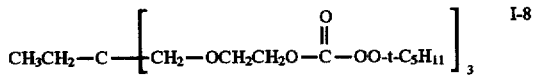

In this example, the product (i.e., 1,1,1-tris[2-(t-amylperoxycarbonyloxy)ethoxymethyl]propane, I-8) was prepared by reacting the polyether tris(chloroformate) of VORANOL® 234–630 (Example 5), t-amyl hydroperoxide and aqueous potassium hydroxide, as described below:

A 200 mL water-jacketed reactor, equipped with a mechanical stirrer, a thermometer and an addition funnel, was charged with 19.6 g (0.070 mole) of 20% aqueous potassium hydroxide solution, 8.0 g (0.070 mole) of 91% t-amyl hydroperoxide and 3 drops (ca. 0.1 g) of TERGITOL® NP-10 at about 20°–25° C. The resulting solution was stirred at about 25° C. To the stirred solution at 24°–32° C. was slowly added 9.3 g (0.020 mole) of 98.7% polyether tris(chloroformate) (from VORANOL® 234–630) over a period of 15 minutes. During the addition, 50 mL of MTBE was added. The reaction mass was then stirred for 3.0 hours at about 30° C. At the end of the reaction period, an additional 50 mL of MTBE was added and, after stirring for an additional 2 minutes, the reaction mass was allowed to separate into liquid phases. The lower aqueous layer was then separated and discarded. The organic layer was cooled to 20° C. and was washed with 50 mL of aqueous 20% potassium hydroxide solution. The crude product solution was then washed with 50 mL of aqueous 15% sodium hydrogen sulfite solution. The resulting organic layer was then washed with saturated aqueous sodium hydrogen carbonate solution to a pH of about 7. The product solution was dried over 5% by weight of anhydrous MgSO$_4$, and, after separation of the spent desiccant by filtration, the solvent was removed in vacuo leaving 10.8 g (ca. 82.2% of theory, uncorrected) of a colorless liquid product. An IR spectrum of the product showed a major monoperoxycarbonate carbonyl band at 1785 cm$^{-1}$ and a major carbonate band at about 1753 cm$^{-1}$. There was a small OH band in the IR spectrum. The product contained 7.52% active oxygen (theory, 7.31%) according to a peroxyester active oxygen method, therefore, the assay of the product was 79.9% and the corrected yield was 65.7%.

Based on the method of preparation, yield data, and IR spectral data the product obtained in this reaction was the desired title product.

EXAMPLE 10

Preparation of Polyether Tetrakis(mono-t-amylperoxycarbonate), I-9

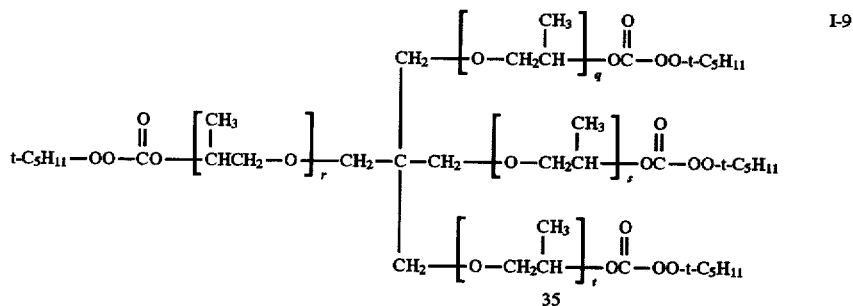

(Where the sum of q, r, s and t is about 6–7)

In this example the product was prepared in two synthetic steps. In the first step polyether tetraol (C-5), (PLURACOL® PeP 550), was reacted with excess phosgene to produce a polyether tetrakis(chloroformate) of Example 7.

In the second step, the polyether tetrakis(chloroformate) was reacted with t-amyl hydroperoxide, in the presence of aqueous potassium hydroxide, to yield the product as described below:

A 250 mL water-jacketed reactor, equipped with a mechanical stirrer, a thermometer and an addition funnel, was charged with 28.1 g (0.10 mole) of 20% aqueous potassium hydroxide solution, 10.1 g (0.09 mole) of 92.6% t-amyl hydroperoxide and 2 drops (ca. 0.1 g) of ALIQUAT® 336 (tricaprylylmethylammonium chloride, manufactured by Henkel Corporation) and the resulting solution was stirred at about 25° C. To the stirred solution at 43°–45° C. was slowly added 15.2 g (0.020 mole) of 100% polyether tetrakis(chloroformate) over a period of 10 minutes. After the addition was completed the reaction mass was stirred for 5 hours at about 35°–40° C. after which 75 mL MTBE was added, the reaction mass was cooled to 25° C., stirred one minute, then allowed to separate into liquid phases. The lower aqueous layer was then separated and the remaining organic layer was washed with 50 mL of aqueous 20% potassium hydroxide solution, then with 50 g of aqueous buffered sodium sulfite solution (made by dissolving 1.2 g of acetic acid, 2.5 g of sodium acetate and 4.3 g of sodium sulfite in 42.0 g of water). The aqueous layer was discarded and the organic layer was washed with 100 g of saturated sodium chloride solution. The product solution was dried over 5% by weight of anhydrous MgSO$_4$, and, after separation of the spent desiccant by filtration, the solvent was removed in vacuo leaving 18.0 g (88.2% of theory, uncorrected) of a colorless liquid. The product contained 5.56% active oxygen (theory, 6.27%) according to a peroxyester active oxygen method, therefore, the assay of the product was 88.7% and the corrected yield was 80.0%.

Based on the method of preparation, yield data, the product obtained in this reaction was the desired title product.

EXAMPLE 11

Preparation of Polyether Tris(mono-t-butylperoxycarbonate), I-10, from PLURACOL® TP-740

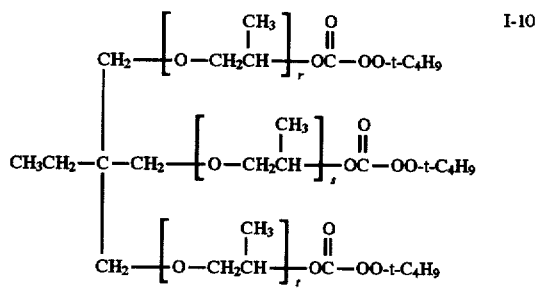

(Where the sum of r, s and t is about 6–7)

In this example the product was prepared in two synthetic steps. In the first step 0.06 mole of polyether triol (C-7),

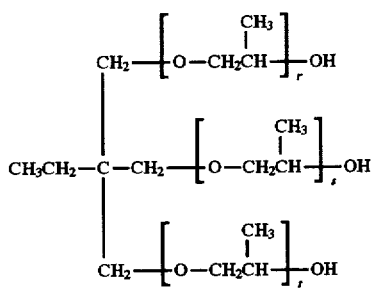

(Where the sum r, s and t is about 10–11) (PLURACOL® TP-740; molecular weight=730; manufactured by BASF Corporation), was reacted with excess phosgene (0.28 mole) at 3°–7° C. The reaction mixture was then stirred for 2–3 hours at 10°–20° C. and allowed to stand overnight at 20°–25° C. The excess phosgene was then stripped from the product at 20°–30° C. and at reduced pressure to produce polyether tris(chloroformate) A, a clear liquid, having an assay of 100% and in a corrected yield of 93.8%.

In the second step, polyether tris(chloroformate) A was reacted with t-butyl hydroperoxide, in the presence of aqueous potassium hydroxide, to yield the product as described below:

A 250 mL water-jacketed reactor, equipped with a mechanical stirrer, a thermometer and an addition funnel, was charged with 19.6 g (0.07 mole) of 25% aqueous potassium hydroxide solution and 9.0 g (0.07 mole) of aqueous 70% t-butyl hydroperoxide at 22°–29° C. The resulting solution was stirred at about 25° C. To the stirred solution at 33°–40° C. was slowly added 18.3 g (0.02 mole) of 100% polyether tris(chloroformate) A over a period of 15 minutes. After the addition was completed the reaction mass was stirred for 1.5 hours at 40° C. after which 17 g of ethylbenzene (EB) was added and the reaction mass was stirred two minutes at about 30° C., then allowed to separate into liquid phases. The lower aqueous layer was then separated and the remaining organic layer was cooled to 25° C. and was washed with 50 g of aqueous 20% potassium hydroxide solution, then washed with 50 g of aqueous buffered sodium sulfite solution (made by dissolving 1.2 g of acetic acid, 2.5 g of sodium acetate and 4.3 g of sodium sulfite in 42.0 g of water) and with 50 g of saturated sodium chloride solution. The product solution was dried over 1.7 g of anhydrous MgSO$_4$, and, after separation of the spent desiccant by filtration, 35.7 g of a colorless liquid was obtained. The product solution contained 2.49% active oxygen (theory, 4.45%) according to a peroxyester active oxygen method, therefore, the assay of the product was 55.96% and the corrected yield was 92.4%.

Based on the method of preparation and yield data the product obtained in this reaction was the desired title product as a 55.9% solution in EB.

EXAMPLE 12

Preparation of Polyether Tris(mono-t-butylperoxycarbonate), I-11, from PLURACOL® GP-730

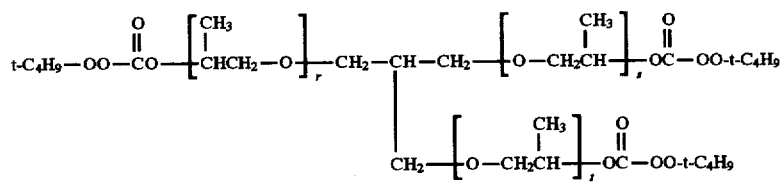

(Where the sum of r, s and t is about 10–11)

In this example the product was prepared in two synthetic steps. In the first step 0.05 mole of polyether triol (C-8),

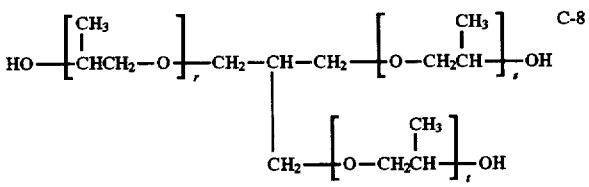

(Where the sum of q, r, s and t is about 10–11) (PLURACOL® GP-730; molecular weight=730; manufactured by BASF Corporation), was reacted with excess phosgene (0.40 mole) at 3°–7° C. The reaction mixture was then stirred for 2–3 hours at 10°–20° C. and allowed to stand overnight at 20°–25° C. The excess phosgene was then stripped from the product at 20°–30° C. and at reduced pressure to produce polyether tris(chloroformate) B, a clear liquid, having an assay of 100% and in a corrected yield of 96.3%.

In the second step, polyether tris(chloroformate) B was reacted with t-butyl hydroperoxide, in the presence of aqueous potassium hydroxide, to yield the product as described below:

A 250 mL water-jacketed reactor, equipped with a mechanical stirrer, a thermometer and an addition funnel, was charged with 19.6 g (0.07 mole) of 25% aqueous potassium hydroxide solution and 9.0 g (0.07 mole) of aqueous 70% t-butyl hydroperoxide at 22°–29° C. The resulting solution was stirred at about 25° C. To the stirred solution at 23°–28° C. was slowly added 18.3 g (0.02 mole) of 100% polyether tris(chloroformate) B over a period of 15 minutes. After the addition was completed the reaction mass was stirred for 3 hours at 25°–30° C. after which 100 mL MTBE was added and the reaction mass was stirred one minute at about 30° C., then allowed to separate into liquid phases. The lower aqueous layer was then separated and the remaining organic layer was cooled to 12° C. and was washed with 50 mL of aqueous 10% sodium hydrogen sulfite solution, then washed with 50 mL of aqueous 10% potassium hydroxide solution and with 50 mL portions of saturated aqueous sodium sulfate solution until the pH was 7–8. The product solution was dried over 5% by weight of anhydrous $MgSO_4$, and, after separation of the spent desiccant by filtration, the solvent was removed in vacuo leaving 20.3 g (94% of theory, uncorrected) of a colorless liquid. The product contained 4.23% active oxygen (theory, 4.45%) according to a peroxyester active oxygen method, therefore, the assay of the product was 95.1% and the corrected yield was 89.3%.

Based on the method of preparation and yield data, the product obtained in this reaction was the desired title product.

EXAMPLE 13

Preparation of 1,5-Bis(1,1,4-trimethyl-4-(t-butylperoxy)pentylperoxycarbonyloxy)-3-oxapentane, I-12

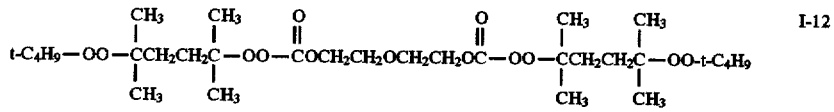

In this example the product was prepared by reacting diethylene glycol bis(chloroformate) (C-9) with

1,1,4-trimethyl-4-(t-butylperoxy)pentyl hydroperoxide (C-10)

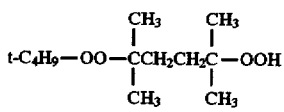

and aqueous potassium hydroxide, to yield the product as described below:

A 250 mL water-jacketed reactor, equipped with a mechanical stirrer, a thermometer and an addition funnel, was charged with 8.0 g (0.05 mole) of 25% aqueous sodium hydroxide solution and 11.0 g (0.043 mole) of 91% 1,1,4-trimethyl-4-(t-butylperoxy)pentyl hydroperoxide at 22°–29° C. The resulting solution was stirred at about 25° C. To the stirred solution at 23°–28° C. was slowly added 5.8 g (0.025 mole) of 99% diethylene glycol bis(chloroformate) (C-9) over a period of 15 minutes. After the addition was completed the reaction mass was stirred for 3.5 hours at 30°–35° C. after which 50 mL MTBE was added and the reaction mass was stirred one minute at about 30° C., then allowed to separate into liquid phases. The lower aqueous layer was then separated and the remaining organic layer was cooled to 17° C. and was washed with 50 mL of aqueous 10% sodium hydrogen sulfite solution, then washed with 50 mL of aqueous 20% sodium hydroxide solution and with 50 mL portions of saturated aqueous sodium sulfate solution until the pH was 7–8. The product solution was dried over 5% by weight of anhydrous $MgSO_4$, and, after separation of the spent desiccant by filtration, the solvent was removed in vacuo leaving 14.7 g (88.6% of theory, uncorrected) of a colorless liquid. An IR spectrum of the product showed a major monoperoxycarbonate carbonyl band at 1785 $cm^{-1}$ and a major carbonate or ester carbonyl band at about 1752 $cm^{-1}$. There was only a trace of an OH band in the IR spectrum. The product contained 4.48% active oxygen (theory, 5.10%) according to a peroxyester active oxygen method, therefore, the assay of the product was 87.0% and the corrected yield was 77.0%.

Based on the method of preparation, yield data, and IR spectral data the product obtained in this reaction was the desired title product.

EXAMPLE 14

280° F. (138° C.) SPI Exotherm Data for Polycaprolactone Tris(mono-t-butylperoxycarbonate), I-4

The unsaturated polyester resin composition employed in this example was a mixture of an unsaturated polyester and styrene monomer. The unsaturated polyester was an alkyd resin made by esterifying the following components:

| COMPONENT | QUANTITY (MOLES) |
| --- | --- |
| Maleic Anhydride | 1.0 |
| Phthalic Anhydride | 1.0 |
| Propylene Glycol | 2.2 |

0.013% by weight of hydroquinone inhibitor was added to the resulting resin. The alkyd resin had an Acid No. of 45–50. Seven (7) parts by weight of the above unsaturated polyester alkyd resin were diluted with three (3) parts by weight of styrene monomer. The resulting unsaturated polyester resin composition had the following properties:

Viscosity (Brookfield No. 2 at 20 r.p.m.)—13.0 poise

Specific Gravity—1.14

Gelation and cure characteristics of t-butyl peroxybenzoate (A-2), (a commercial peroxide product used to cure unsaturated polyester resin compositions), and polycaprolactone tris(mono-t-butylperoxycarbonate), I-4, a novel poly(monoperoxycarbonate) composition of the instant invention, were determined using the Standard SPI Exotherm Procedure (Suggested SPI Procedure for Running Exotherm Curves-Polyester Resins, published in the Preprint of the 24th Annual Technical Conference—Reinforced Plastics/Composites Division, Society of the Plastics Industry, Inc., 1969). Using this procedure at 28° F. (138°

C.), A-2 and I-4 were comparatively evaluated. The amount of I-4 employed was equivalent in active oxygen content to 1.0 g of pure A-2 per 100 g of unsaturated polyester resin. The results of this investigation are given in Example 14 Table and showed that I-4 gelled and cured the resin much more rapidly than A-2, hence, I-4 was more active in curing the unsaturated polyester resin than was the commercial peroxide catalyst A-2.

EXAMPLE 14 TABLE
280° F. (138° C.) SPI EXOTHERM DATA

| CURING AGENT | G/100 G RESIN | GEL, MINS. | CURE, MINS. | PEAK EXO, °F. | BARCOL HARDNESS |
|---|---|---|---|---|---|
| I-4 | 1.64 | 0.9 | 1.85 | 428 | 35–40 |
| A-2 | 1.0 | 1.3 | 2.0 | 443 | 40–45 |

EXAMPLE 15

Enhanced Polymerizations of Styrene Employing Novel Tris- and Poly(monoperoxycarbonate) Compositions as Free-Radical Initiators Styrene polymerizations were carried out using a monomer solution containing 95% styrene and 5% ethylbenzene (EB).

Initiators employed were 1,1-di(t-butylperoxy) cyclohexane (A-3), i.e., Lupersol 331 (manufactured by Elf Atochem North America, Inc.; the commercial initiator used currently to produce high molecular weight polystyrene at enhanced polymerization rates), 1,5-bis(t-butylperoxycarbonyloxy)-5-oxapentane (A-4; a bis (monoperoxycarbonate) composition of the art; U.S. Pat. No. 3,652,631), polycaprolactone bis(mono-t-butylperoxycarbonate) (A-1) (a bis(monoperoxycarbonate) composition of the art; U.S. Pat. No. 5,314,970) and several poly(monoperoxycarbonate) compositions of the instant invention, i.e., 1,1,1-tris(t-butylperoxycarbonyloxymethyl) ethane (I-1), 1,1,1-tris(t-butylperoxycarbonyloxymethyl) propane (I-2), polycaprolactone tris(mono-t-butylperoxycarbonate) (I-3), polycaprolactone tris(mono-t-butylperoxycarbonate) (I-4), 1,1,1-tris[2-(t-butylperoxycarbonyloxy)ethoxymethyl]propane (I-5) and polycaprolactone tetrakis(mono-t-butylperoxycarbonate) (I-6).

Preparation of Styrene/Initiator Solutions

To solutions of 95% styrene and 5% ethylbenzene at room temperature were added levels of free-radical initiators equal to 0.00277 mole of active oxygen per 1000 g of styrene solution (or 0.00252 mole of active oxygen per liter of styrene solution). The resulting styrene solutions were purged with nitrogen prior to being sealed in glass ampules (10 mm O.D., 8 mm I.D.).

Styrene Polymerization Procedure

Ampules containing the styrene solutions (several for each solution) were immersed in a circulating oil bath in which the temperature was regulated through a temperature programmer unit. Samples were subjected to a 100° C. to 151° C. linear temperature ramp, at a programmed rate of 0.17° C./minute (5-hour program). Samples of each solution were withdrawn from the bath at 1-hour intervals during the 5-hour program and cooled by immersion in an ice-water bath. The styrene solutions were then removed from the ampules and analyzed for polystyrene weight average molecular weight ($M_w$) and residual styrene monomer content.

Results

The performances of tris(mono-t-butylperoxycarbonates) I-1, I-2, I-3, I-4, and I-5 tetrakis(mono-t-butylperoxycarbonate) I-6 were compared to art compositions A-1, A-3 and A-4 according to the above-described methodology. The results obtained are summarized 5 Table:

EXAMPLE 15 TABLE - STYRENE POLYMERIZATIONS

| Initiator (Level, ppm)* | Polym. Time, hours | Polystyrene Weight Ave. Molecular Weight, $M_w$ | Residual Styrene Monomer, % |
|---|---|---|---|
| A-3 (361) | 1 | 244,000 | 82.8 |
|  | 2 | 245,000 | 65.0 |
|  | 3 | 285,000 | 42.3 |
|  | 4 | 293,000 | 26.9 |
|  | 5 | 278,000 | 17.8 |
| A-4 (469) | 1 | 285,000 | 83.2 |
|  | 2 | 274,000 | 67.8 |
|  | 3 | 294,000 | 43.8 |
|  | 4 | 307,000 | 18.9 |
|  | 5 | 297,000 | 12.0 |
| A-1 (1062) | 3 | 294,000 | 39.2 |
|  | 5 | 288,000 | 10.6 |
| I-1 (433) | 1 | 298,000 | 85.1 |
|  | 2 | 306,000 | 68.9 |
|  | 3 | 356,000 | 43.1 |
|  | 4 | 371,000 | 20.6 |
|  | 5 | 348,000 | 12.1 |

EXAMPLE 15 TABLE - STYRENE POLYMERIZATIONS

| Initiator (Level, ppm)* | Polym. Time, hours | Polystyrene Weight Ave. Molecular Weight, $M_w$ | Residual Styrene Monomer, % |
|---|---|---|---|
| I-2 (446) | 1 | 274,000 | 84.6 |
|  | 2 | 291,000 | 68.6 |
|  | 3 | 335,000 | 42.0 |
|  | 4 | 343,000 | 19.0 |
|  | 5 | 339,000 | 11.5 |
| I-3 (599) | 3 | 357,000 | 41.8 |
|  | 5 | 356,000 | 10.1 |
| I-4 (821) | 1 | 303,000 | 80.6 |
|  | 2 | 304,000 | 69.7 |
|  | 3 | 362,000 | 39.0 |
|  | 4 | 390,000 | 16.4 |
|  | 5 | 374,000 | 10.1 |
| I-5 (568) | 3 | 354,000 | 40.5 |
|  | 5 | 347,000 | 10.4 |
| I-6 (1019) | 1 | 240,000 | 81.8 |
|  | 2 | 245,000 | 61.1 |
|  | 3 | 306,000 | 27.3 |
|  | 4 | 339,000 | 9.7 |
|  | 5 | 331,000 | 5.0 |

*Parts per million parts of styrene solution.

Based on polystyrene weight average weight ($M_w$) results, use of the tris- and poly(monoperoxycarbonate) compositions of the instant invention i.e. I-1, I-2, I-3, I-4, I-5, and I-6, as styrene polymerization initiators resulted in significantly higher $M_w$ values (330,000 to 375,000) after the 5-hour polymerization program than were obtained with art compositions A-1 ($M_w$, ca. 290,000), A-3 ($M_w$, ca. 280,000) and A-4 ($M_w$, ca. 300,000). A-1 (a bis(monoperoxycarbonate) composition of the art) was considerably less effective in enhancing the molecular weight of polystyrene (maximum $M_w$ was ca. 290,000) than were the tris- and poly (monoperoxycarbonate) compositions of the instant invention ($M_w$ ca. 330,000 to 375,000). Thus, the tris- and poly(monoperoxycarbonate) compositions of the instant invention significantly advance the art of polymerizing ethylenically unsaturated monomers such as styrene.

EXAMPLE 16

Enhanced Polymerizations of Styrene Employing Novel Tris- and Poly(monoperoxycarbonate) Compositions as Free-Radical Initiators Styrene polymerizations were carried out using the procedure outlined in Example 15. Evaluated as free-radical initiators compared to 1,1-di(t-butylperoxy)cyclohexane (A-3) were several additional poly(monoperoxycarbonates) of Structure A: polyether tetrakis(mono-t-butylperoxycarbonate) (I-7), polyether tetrakis(mono-t-amylperoxycarbonate) (I-9), polyether tris(mono-t-butylperoxycarbonate) (I-10) from PLURACOL® TP-740, polyether tris(mono-t-butylperoxycarbonate) (I-11) from PLURACOL® GP-730 and 1,5-bis(1,1,4-trimethyl-4-(t-butylperoxy)pentylperoxycarbonyloxy)-3-oxapentane (I-12). The levels of free-radical initiators employed in this example were equal to 0.00277 mole of active oxygen per 1000 g of styrene solution (or 0.00252 mole of active oxygen per liter of styrene solution).

Styrene Polymerization Procedure

Ampules containing the styrene solutions (several for each solution) were immersed in a circulating oil bath in which the temperature was regulated through a temperature programmer unit. Samples were subjected to a 100° C. to 151° C. linear temperature ramp, at a programmed rate of 0.17° C./minute (5-hour program). Samples of each solution were withdrawn from the bath at 1-hour intervals during the 5-hour program and cooled by immersion in an ice-water bath. The styrene solutions were then removed from the ampules and analyzed for polystyrene weight-average molecule weight ($M_w$) and residual styrene monomer content.

Results

The performances of poly(monoperoxycarbonates) I-7, I-9, I-10, I-11, and I-12 were compared to art composition A-3 according to the above-described methodology. The results obtained are summarized below in Example 16 Table:

EXAMPLE 15 TABLE - STYRENE POLYMERIZATIONS

| Initiator (Level, ppm)* | Polym. Time, hours | Polystyrene Weight Ave. Molecular Weight, $M_w$ | Residual Styrene Monomer, % |
|---|---|---|---|
| A-3 (361) | 1 | 244,000 | 82.8 |
| | 2 | 245,000 | 65.0 |
| | 3 | 285,000 | 42.3 |
| | 4 | 293,000 | 26.9 |
| | 5 | 278,000 | 17.8 |
| I-7 (669) | 3 | 400,000 | 37.5 |
| | 5 | 391,000 | 10.3 |
| I-9 (707) | 1 | 254,000 | 80.1 |
| | 3 | 368,000 | 31.8 |
| | 4 | 354,000 | 17.3 |
| | 5 | 341,000 | 10.5 |
| I-10 (997) | 1 | 262,000 | 82.8 |
| | 2 | 270,000 | 67.6 |
| | 3 | 322,000 | 32.3 |
| | 4 | 328,000 | 14.9 |
| | 5 | 318,000 | 9.0 |
| I-11 (997) | 1 | 259,000 | 89.4 |
| | 2 | 273,000 | 71.5 |
| | 3 | 317,000 | 35.4 |
| | 4 | 332,000 | 15.6 |
| | 5 | 318,000 | 9.4 |
| I-12 (435) | 3 | 304,000 | 50.3 |
| | 5 | 297,000 | 5.5 |

Based on polystyrene weight-average molecular weight ($M_w$) results, use of the poly(monoperoxycarbonate) compositions of the instant invention, i.e., I-7, I-9, I-10, I-11 and I-12, as styrene polymerization initiators resulted in significantly higher $M_w$ values (ca. 300,000 to 390,000) after the 5-hour polymerization program than were obtained with art A-3 ($M_w$, ca. 280,000). In addition, at the end of 5 hours, the residual styrene levels for styrenes produced by the novel poly(monoperoxycarbonate) compositions of the instant invention were significantly lower than the polystyrene produced by A-3 (5–10% residual styrene versus 17–18% residual styrene). I-12 was especially attractive in this respect. These results show that the poly(monoperoxycarbonate) compositions of the instant invention significantly advance the art of polymerizing ethylenically unsaturated monomers such as styrene.

EXAMPLE 17

Enhanced Polymerizations of Styrene Employing Poly(monoperoxycarbonate) Compositions in Combination with 1,1-di(t-butylperoxy)cyclohexane (A-3)

Styrene polymerizations were carried out using a monomer solution containing 95% styrene and 5% ethylbenzene (EB). The polymerization methodology employed in this example was a modification of the procedure outlined in Example 15. In this example, combinations of two free-radical initiators were employed in which one of the initiators of the combination was a novel poly(monoperoxycarbonate) of the instant invention i.e., 1,1,1-tris[2-(t-butyl-peroxycarbonyloxy)ethoxymethyl]propane (I-5) or polyether tetrakis(mono-t-butylperoxycarbonate) (I-7). The second initiator of the initiator combinations was 1,1-di(t-butylperoxy)cyclohexane (A-3), an art composition.

Preparation of Styrene/Initiator Solutions

The levels of the combinations of free-radical initiators employed in this example were equal to a total of 0.00230 mole of active oxygen per 1000 g of styrene solution (or 0.00209 mole of active oxygen per liter of styrene solution).

Styrene Polymerization Procedure

Ampules containing the styrene solutions (several for each solution) were immersed in a circulating oil bath in which the temperature was regulated through a temperature programmer unit. Samples were subjected to a 100° C. to 145.6° C. linear temperature ramp, at a programmed rate of 0.19° C./minute (4-hour program). At the end of the 4-hour period the samples were withdrawn from the bath and cooled by immersion in an ice-water bath. The styrene solutions were then removed from the ampules and analyzed for polystyrene weight-average molecular weight ($M_w$).

Results

Example 17 Table summarizes the polystyrene weight average molecular weights that were obtained when Initiator Combination A (I-5 and A-3) and Initiator Combination B (I-7 and A-3) were employed as free-radical initiator systems:

EXAMPLE 17 TABLE
STYRENE POLYMERIZATIONS INITIATED BY INITIATOR COMBINATIONS

| INITIATOR COMBINATION A | Mole of Act[O]* from: | | Polystyrene Weight-Average Molecular |
|---|---|---|---|
| (I-5/A-3) | I-5 | A-3 | Weight, $M_w$ |
| | 0.0 | 0.00230 | 267,000 |
| | 0.00092 | 0.00138 | 277,000 |
| | 0.00138 | 0.00092 | 288,000 |
| | 0.00184 | 0.00046 | 303,000 |
| | 0.00230 | 0.0 | 319,000 |

| INITIATOR COMBINATION B | Mole of Act[O]* from: | | Polystyrene Weight-Average Molecular |
|---|---|---|---|
| (I-7/A-3) | I-7 | A-3 | Weight, $M_w$ |
| | 0.0 | 0.00230 | 267,000 |
| | 0.00092 | 0.00138 | 290,000 |
| | 0.00138 | 0.00092 | 310,000 |
| | 0.00184 | 0.00046 | 328,000 |
| | 0.00230 | 0.0 | 355,000 |

*Per 1000 g of 95% styrene/5% Ethylbenzene solution; Total level of initiator in combination was equal to 0.00230 mole of active oxygen.

The results show that the polystyrene weight-average molecular weight can be adjusted upward by replacing some of initiator A-3 with either I-5 or I-7, or adjusted downward by replacing some of either I-5 or I-7 with initiator A-3. Hence, polystyrene producers can use the novel poly (monoperoxycarbonates) of the instant invention in Combination with other free-radical initiators in order to adjust the molecular weight of polystyrene, thus adjusting the physical properties of polystyrene.

EXAMPLE 18

Enhanced Polymerizations of Styrene Employing Polyether Tetrakis(mono-t-butylperoxycarbonate) (I-7) in Combination with t-Butyl Peroxybenzoate (A-2)

Styrene polymerizations were carried out using a monomer solution containing 95% styrene and 5% ethylbenzene (EB). The polymerization methodology employed in this example was a modification of the procedure outlined in Example 15. In this example, a combinations of two free-radical initiators was employed in which one of the initiators of the combination was a novel poly(monoperoxycarbonate) of the instant invention i.e., polyether tetrakis(mono-t-butylperoxycarbonate) (I-7) and the second initiator of the initiator combinations was an art monoperoxide, i.e., t-butyl peroxybenzoate (A-2).

Preparation of Styrene/Initiator Solutions

The total levels of free-radical initiators employed in this example were equal to a total of 0.00277 mole of active oxygen per 1000 g of styrene solution (or 0.00230 mole of active oxygen per liter of styrene solution).

Styrene Polymerization Procedure

Ampules containing the styrene solutions (several for each solution) were immersed in a circulating oil bath in which the temperature was regulated through a temperature programmer unit. Samples were subjected to a 100° C. to 151° C. linear temperature ramp, at a programmed rate of 0.17° C./minute (5-hour program). At the end of the 5-hour period the samples were withdrawn from the bath and cooled by immersion in an ice-water bath. The styrene solutions were then removed from the ampules and analyzed for polystyrene weight-average molecular weight ($M_w$).

Results

Example 18 Table summarizes the polystyrene weight average molecular weights that were obtained when Initiator Combination C (I-7 and A-2) was employed as a free-radical initiator system:

EXAMPLE 18 TABLE
STYRENE POLYMERIZATIONS INITIATED BY INITIATOR COMBINATIONS

| INITIATOR COMBINATION C | Mole of Act[O]* from: | | Polystyrene Weight-Average Molecular |
|---|---|---|---|
| (I-7/A-2) | I-7 | A-2 | Weight, $M_w$ |
| | 0.0 | 0.00277 | 212,000 |
| | 0.001385 | 0.001385 | 279,000 |
| | 0.00277 | 0.0 | 391,000 |

| A-3 | Mole of Act[O]* from: | Polystyrene Weight-Average Molecular Weight, $M_w$ |
|---|---|---|
| | 0.00277 | 278,000 |

*Per 1000 g of 95% styrene/5% Ethylbenzene solution; Total level of initiator in combination was equal to 0.00277 mole of active oxygen.

The results in Example 18 Table show that the polystyrene weight-average molecular weight can be adjusted upward by replacing some of art monoperoxide A-2 with I-7, or adjusted downward by replacing some of I-7 with art monoperoxide A-2. Hence, polystyrene producers can use the novel poly(monoperoxycarbonates) of the instant invention in combination with other monoperoxide initiators in order to adjust the molecular weight of polystyrene, thus adjusting the physical properties of polystyrene.

The subject matter which the applicants regard as their invention is particularly pointed out and distinctly claimed as follows:

We claim:

1. A novel poly(monoperoxycarbonate) of Structure A:

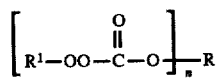

where n is an integer from 3 to 8, $R^1$ is selected from the group consisting of t-alkyl radicals of 4 to 12 carbons, 1,1,4-trimethyl-4(t-butylperoxy)pentyl radical, 1,1,4-trimethyl-4(t-amylperoxy)pentyl radical, t-cycloalkyl radicals of 6 to 10 carbons, t-aralkyl radicals of 9 to 13 carbons and 3-methyl-1-butyn-3-yl and 3-methyl-1-pentyn-3-yl, and with the proviso that when $R^1$ is selected from 1,1,4-trimethyl-4(t-butylperoxy)pentyl radical and 1,1,4-trimethyl-4(t-amylperoxy)pentyl radical, n can also have a value of 2;

when n is 2, R is a diradical selected from alkylene of 2 to 12 carbons, alkenylene of 4 to 8 carbons and diradical structures (n) and (o),

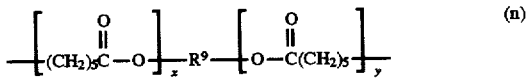

-continued $$-\left[\begin{array}{cc} R^4 & R^5 \\ | & | \\ CH-CH-O \end{array}\right]_r R^9 \left[\begin{array}{cc} R^5 & R^4 \\ | & | \\ O-CH-CH \end{array}\right]_s-$$ (o)

where $R^9$ is an alkylene diradical of 2 to 8 carbons;

when n is 3, R is a triradical selected from 1,3,5-cyclohextriyl, $R^2C(CH_2-)_3$, $-CHR^2CH(-)CH_2-$ and structures (a), (b), (c), (d) and (e), $$-CH_2-CH-CH_2CH_2-,$$ (a)

$$-CH_2-CH-CH_2CH_2CH_2CH_2-,$$ (b)

$$-\left[(CH_2)_5 C-O\right]_x R^3 \left[O-\overset{O}{\underset{\|}{C}}(CH_2)_5\right]_y,$$ (c)

$$\left[O-\overset{O}{\underset{\|}{C}}(CH_2)_5\right]_z$$

$$-\left[\begin{array}{cc} R^4 & R^5 \\ | & | \\ CH-CH-O \end{array}\right]_r R^3 \left[\begin{array}{cc} R^5 & R^4 \\ | & | \\ O-CH-CH \end{array}\right]_s,$$ (d)

$$\left[\begin{array}{cc} R^5 & R^4 \\ | & | \\ O-CH-CH \end{array}\right]_t$$

$$\begin{array}{c} R^4 \quad R^5 \\ | \quad | \\ -CH-CH-N \end{array} \begin{array}{c} R^5 \quad R^4 \\ | \quad | \\ -CH-CH- \\ R^5 \quad R^4 \\ | \quad | \\ -CH-CH- \end{array}$$ (e)

where $R^2$ is selected from hydrogen and an alkyl radical of 1 to 6 carbons, $R^3$ is a triradical selected from the group consisting of $R^2C(CH_2-)_3$, $-CHR^2CH(-)CH_2-$ and structures (a) and (b), $R^4$ and $R^5$ are the same or different and are selected from hydrogen and alkyl radicals of 1 to 4 carbons, x, y and z are integers from 0 to 5 with the proviso that the sum of x, y and z is from 2 to 8, and r, s and t are integers from 0 to 6 with the proviso that the sum of r, s and t is from 3 to 18, and when n is 4 to 8, R is a polyradical selected from $C(CH_2-)_4$ and structures (f), (g), (h), (i), (j), (k) and (l), $$-CH_2-CH-CH-CH_2-,$$ (f)

$$\begin{array}{c} -CH_2 \\ | \\ -CH_2-C-CH_2-O-CH_2-C-CH_2-, \\ | \\ -CH_2 \end{array} \begin{array}{c} CH_2- \\ | \\ CH_2- \end{array}$$ (g)

$$-\left[O-\overset{O}{\underset{\|}{C}}(CH_2)_5\right]_v$$ (h)

$$-\left[(CH_2)_5 C-O\right]_x R^6 \left[O-\overset{O}{\underset{\|}{C}}(CH_2)_5\right]_y,$$

$$\left[O-\overset{O}{\underset{\|}{C}}(CH_2)_5\right]_z$$

$$-\left[\begin{array}{cc} R^5 & R^4 \\ | & | \\ O-CH-CH \end{array}\right]_q$$ (i)

$$-\left[\begin{array}{cc} R^4 & R^5 \\ | & | \\ CH-CH-O \end{array}\right]_r R^6 \left[\begin{array}{cc} R^5 & R^4 \\ | & | \\ O-CH-CH \end{array}\right]_s,$$

$$\left[\begin{array}{cc} R^5 & R^4 \\ | & | \\ O-CH-CH \end{array}\right]_t$$

$$\begin{array}{c} R^4 \quad R^5 \\ | \quad | \\ -CH-CH- \\ R^4 \quad R^5 \\ | \quad | \\ -CH-CH- \end{array} N-R^7-N \begin{array}{c} R^5 \quad R^4 \\ | \quad | \\ -CH-CH- \\ R^5 \quad R^4 \\ | \quad | \\ -CH-CH- \end{array}$$ (j)

$$\begin{array}{ccc} -CH_2 & CH_2- & CH_2- \\ | & | & | \\ -CH_2-C-CH_2-O-CH_2-C-CH_2-O-CH_2-C-CH_2-, \\ | & | & | \\ -CH_2 & CH_2- & CH_2- \end{array}$$ (k)

$$R^8 \left\{ \left[\begin{array}{cc} R^5 & R^4 \\ | & | \\ O-CH-CH \end{array}\right]_p \right\}_8$$ (l)

where $R^6$ is a tetraradical selected from $C(CH_2-)_4$ and structure (f), $R^7$ is a diradical selected from alkylene of 2 to 6 carbons and 1,2-, 1,3- and 1,4-phenylene, $R^8$ is the sucrose-based octaradical of structure (m), $$\begin{array}{c} -CH_2 \\ \diagdown \\ CH-O \\ -CH \diagdown \quad CH-O-CH-O \\ -CH-CH- \quad -CH \quad CH-CH_2- \\ \diagdown \\ CH- \end{array} \begin{array}{c} CH_2- \\ | \\ -CH-O \\ | \\ \end{array}$$ (m)

p is an integer from 1 to 3, v is an integer from 0 to 5 with the proviso that the sum of v, x, y and z is from 3 to 10, and q is an integer from 0 to 4 with the proviso that the sum of q, r, s and t is from 2 to 16 and with the further proviso that when R is $R^3C(CH_2-)_3$, structure (b) or $C(CH_2-)_4$, $R^1$ is t-butyl.

2. A poly(monoperoxycarbonate) as defined in claim 1 wherein when n is 3, R is a triradical selected from 1,3,5-cyclohextriyl, $R^2C(CH_2-)_3$, $-CHR^2CH(-)CH_2-$, and structures (a), (b), (d) and (e).

3. A poly(monoperoxycarbonate) as defined in claim 1 wherein when n is 4 to 8, R is a polyradical selected from $C(CH_2-)_4$ and structures (f), (g), (i), (j), (k) and (l).

4. A poly(monoperoxycarbonate) as defined in claim 1 selected from the group consisting of: 1,1,1-tris(t- butylperoxycarbonyloxymethyl)ethane, 1,1,1-tris-(t-butylperoxycarbonyloxymethyl)propane, polycaprolactone tris(mono-t-butylperoxycarbonates) of molecular weight of about 600 to about 1300, polyether tris(mono-t-butylperoxycarbonates) and polyether tris(mono-t-amylperoxycarbonates) of molecular weight of about 600 to about 1200, polycaprolactone tetrakis(mono-t-butylperoxycarbonates) of molecular weight of about 1500, polyether tetrakis(mono-t-butylperoxycarbonates) and polyether tetrakis(mono-t-amylperoxycarbonates) of molecular weight of about 800 to about 1100, and 1,5-bis(1,1,4-trimethyl-4-(t-butylperoxy)pentylperoxycarbonyloxy)-3-oxapentane.

5. A poly(monoperoxycarbonate) as defined in claim 1 wherein n is 3 or 4.

6. A poly(monoperoxycarbonate) as defined in claim 5 wherein R is selected from the group consisting of $R^2C(CH_2—)_3$ and $C(CH_2—)_4$ and structures (a), (c), (d), (h) and (i).

7. A poly(monoperoxycarbonate) as defined in claim 6 wherein $R^1$ is selected from t-butyl and t-amyl.

8. A poly(monoperoxycarbonate) as defined in claim 7 wherein R is structure (c).

9. A poly(monoperoxycarbonate) as defined in claim 7 wherein R is structure (d).

10. A poly(monoperoxycarbonate) as defined in claim 7 wherein R is structure (h).

11. A poly(monoperoxycarbonate) as defined in claim 7 wherein R is structure (i).

12. A process for use of one or more poly (monoperoxycarbonate) (s) as defined in claim 1 as (a) free-radical initiator(s), in effective initiating amounts, for the initiation of free-radical reactions selected from the group consisting of:

a. Polymerizing ethylenically unsaturated monomer compositions (such as styrene, ethylene, allyl diglycol carbonate (ADC), and the like known to the art as susceptible to such polymerizations), optionally in the presence of an unsaturated elastomer (such as polybutadiene, polyisoprene, and the like known in the art to be useful when present in such polymerizations);

b. curing of unsaturated polyester resin compositions, c. crosslinking and curing of olefin thermoplastic polymer and elastomeric compositions, and, e. modifying the molecular weight of polyolefin compositions, which comprises heating said substrates in the presence of an effective initiating amount of the peroxide composition for a time sufficient to at least partially decompose said peroxide, to perform the free-radical reaction.

13. A process as defined in claim 12 for polymerizing styrene monomer.

14. A process as defined in claim 13 wherein the poly (monoperoxycarbonate) composition is selected from the group consisting of: 1,1,1-tris(t-butylperoxycarbonyloxymethyl)ethane, 1,1,1-tris(t-butylperoxycarbonyloxymethyl)propane and polyether tris (mono-t-butylperoxycarbonates) of molecular weight of about 600 to about 1300, polyether tris(mono-t-butylperoxycarbonates) and polyether tris(mono-t-amylperoxycarbonates) of molecular weight of about 600 to about 1200, polycaprolactone tetrakis(mono-t-butylperoxycarbonates) of molecular weight of about 1500, polyether tetrakis(mono-t-butylperoxycarbonates) and polyether tetrakis(mono-t-amylperoxycarbonates) of molecular weight of about 800 to about 1100, and 1,5-bis(1,1,4-trimethyl-4-(t-butylperoxy)pentylperoxycarbonyloxy)-3-oxapentane.

15. A process as defined in claim 12 for curing of an unsaturated polyester resin composition wherein the poly (monoperoxycarbonate) composition is selected from the group consisting of polycaprolactone tris(mono-t-butylperoxycarbonates) of molecular weight of about 600 to about 1300.

16. A process for the use of one or more peroxide compositions of claim 1 in combination with at least one other peroxide or diperoxide selected from the group consisting of diacyl peroxides, diperoxyketals, peroxyesters, monoperoxycarbonates and dialkyl peroxides, in effective initiating amounts, for the initiation of free-radical polymerization of ethylenically unsaturated monomer compositions, optionally in the presence of an unsaturated elastomer, which comprises heating ethylenically unsaturated monomers and optional unsaturated elastomers in the presence of an effective initiating amount of the combination of peroxides for a time sufficient to at least partially decompose said combination of peroxides.

17. A process as defined in claim 16 for polymerizing styrene monomer.

18. A process as defined in claim 17 wherein the poly (monoperoxycarbonate) composition is selected from the group consisting of:

polyether tris(mono-t-butylperoxycarbonates) of molecular weight of about 600 to about 1200 and polyether tetrakis(mono-t-butylperoxycarbonates) of molecular weight of about 800 to about 1100 and the initiator used in combination with the poly(monoperoxycarbonate) composition is selected from the group consisting of diperoxyketals and peroxyesters.

19. A process as defined in claim 18 wherein the diperoxyketal is 1,1-di(t-butylperoxy)cyclohexane.

20. A process as defined in claim 18 wherein the peroxyester is t-butyl peroxybenzoate.

* * * * *